United States Patent
Keller et al.

(10) Patent No.: US 10,561,687 B2
(45) Date of Patent: Feb. 18, 2020

(54) METHODS FOR MAKING AND USING SINOATRIAL NODE-LIKE PACEMAKER CARDIOMYOCYTES AND VENTRICULAR-LIKE CARDIOMYOCYTES

(71) Applicant: UNIVERSITY HEALTH NETWORK, Toronto, Ontario (CA)

(72) Inventors: Gordon Keller, Toronto (CA); Stephanie Protze, Toronto (CA)

(73) Assignee: UNIVERSITY HEALTH NETWORK, Toronto, Ontario (CA)

( * ) Notice: Subject to any disclaimer, the term of this patent is extended or adjusted under 35 U.S.C. 154(b) by 0 days.

(21) Appl. No.: 15/550,572

(22) PCT Filed: Feb. 17, 2016

(86) PCT No.: PCT/CA2016/050142
§ 371 (c)(1),
(2) Date: Aug. 11, 2017

(87) PCT Pub. No.: WO2016/131137
PCT Pub. Date: Aug. 25, 2016

(65) Prior Publication Data
US 2018/0028572 A1   Feb. 1, 2018

Related U.S. Application Data

(60) Provisional application No. 62/117,107, filed on Feb. 17, 2015.

(51) Int. Cl.
*C12N 5/00* (2006.01)
*A61K 35/34* (2015.01)
*C12N 5/077* (2010.01)
*C12N 5/10* (2006.01)

(52) U.S. Cl.
CPC ............ *A61K 35/34* (2013.01); *C12N 5/0657* (2013.01); *C12N 5/10* (2013.01); *C12N 2501/115* (2013.01); *C12N 2501/15* (2013.01); *C12N 2501/155* (2013.01); *C12N 2501/16* (2013.01); *C12N 2501/165* (2013.01); *C12N 2501/385* (2013.01); *C12N 2501/727* (2013.01); *C12N 2501/999* (2013.01); *C12N 2506/02* (2013.01); *C12N 2506/45* (2013.01)

(58) Field of Classification Search
CPC .............................. C12N 5/0657; A61K 35/34
See application file for complete search history.

(56) References Cited

U.S. PATENT DOCUMENTS

| | | | |
|---|---|---|---|
| 5,843,780 A | 12/1998 | Thomson | |
| 5,945,577 A | 8/1999 | Stice et al. | |
| 5,994,619 A | 11/1999 | Stice et al. | |
| 6,200,806 B1 | 3/2001 | Thomson | |
| 6,235,970 B1 | 5/2001 | Stice et al. | |
| 8,058,065 B2 | 11/2011 | Yamanaka et al. | |
| 8,278,104 B2 | 10/2012 | Yamanaka et al. | |
| 2009/0047263 A1 | 2/2009 | Yamanaka et al. | |
| 2009/0068742 A1 | 3/2009 | Yamanaka | |
| 2009/0191159 A1 | 7/2009 | Sakurada et al. | |
| 2009/0227032 A1 | 9/2009 | Yamanaka et al. | |
| 2009/0246875 A1 | 10/2009 | Yamanaka et al. | |
| 2009/0304646 A1 | 12/2009 | Sakurada et al. | |
| 2011/0305672 A1 | 12/2011 | Dalton et al. | |
| 2014/0134733 A1 | 5/2014 | Wu et al. | |

FOREIGN PATENT DOCUMENTS

| WO | 2008/112323 A1 | 9/2008 |
|---|---|---|
| WO | WO 2008/112323 A1 | 9/2008 |
| WO | WO 2015/035506 A1 | 3/2015 |

OTHER PUBLICATIONS

Burridge et al. Nat. Methods. 11(8):855-860, 2014 (Year: 2014).*
Zhu et al. Circ. Res. 107:776-786, 2014 (Year: 2010).*
Davis et al. Mechanisms of Development. 108:105-119, 2001 (Year: 2001).*
Ionta, V. et al., "SHOX2 overexpression favors differentiation of embryonic stem cells into cardiac pacemaker cells, Improving biological pacing ability", Stem Cell Reports, vol. 4, No. 1, 129-142 (2015).
Xu, H. et al., "Highly efficient derivation of ventricular cardiomyocytes from induced pluripotent stem cells with a distinct epigenetic signature", Cell Research, vol. 22, No. 1, 142-154 (2012).
A. Barbutti and R.B. Robinson "Stem cell-derived nodal-like cardiomyocytes as a novel pharmacologic tool: insights from sinoatrial node development and function", Pharmacological Reviews, vol. 67, No. 2, 368-388 (2015).
V. Vedantham "New approaches to biological pacemakers: links to sinoatrial node development", Trends in Molecular Medicine, vol. 21, No. 12, 749-761 (2015).
International Search Report and Written Opinion in International Application No. PCT/CA2016/050142, dated May 2, 2016.
Extended European Search Report from EP Application No. 16751855.4, dated Jun. 20, 2018.
Birket et al., "Expansion and patterning of cardiovascular progenitors derived from human pluripotent stem cells", Nature Biotechnology, 2015, vol. 33, No. 9, pp. 970-979.
Spater et al., "A HCN4+ cardiomyogenic progenitor derived from the first heart field and human pluripotent stem cells", Nature Cell Biology, 2013, vol. 15, No. 9, pp. 1098-1106.
Zhang et al., "Direct differentiation of atrial and ventricular myocytes from human embryonic stem cells by alternating retinoid signals", Cell Research, 2010, vol. 21, No. 4, pp. 579-587.
Matthew J. Birket et al., "Expansion and patterning of cardiovascular progenitors derived from human pluripotent stem cells", Nature Biotechnology, Sep. 1, 2015, pp. 970-979, vol. 33, No. 9.

(Continued)

*Primary Examiner* — Marcia S Noble
(74) *Attorney, Agent, or Firm* — Proskauer Rose LLP

(57) ABSTRACT

Provided are methods for producing compositions comprising a population of cardiomyocytes enriched for or substantially devoid of sinoatrial node-like pacemaker cardiomyocytes (SANLCM) from human pluripotent stem cells (hPSCs), and methods of use thereof.

22 Claims, 12 Drawing Sheets

Specification includes a Sequence Listing.

(56) References Cited

OTHER PUBLICATIONS

Daniela Spater et al., "A HCN4+ cardiomyogenic progenitor derived from the first heart field and human pluripotent stem cells", Nature—Cell Biology, Sep. 2013, pp. 1098-1115, vol. 15, No. 9.
Qiangzhe Zhang et al., "Direct differentiation of atrial and ventricular myocytes from human embryonic stem cells by alternating retinoid signals", Cell Research, Nov. 23, 2010 (online), 579-587, vol. 21, No. 4.
Steven J. Kattman et al., "Stage-Specific Optimization of Activin/Nodal and BMP Signaling Promotes Cardiac Differentiation of Mouse and Human Pluripotent Stem Cell Lines," Cell Stem Cell, 2011, vol. 8, pp. 228-240.
L. Yang et al., "Human cardiovascular progenitor cells develop from a KDR+ embryonic-stem-cell-derived population," Nature, 2008, vol. 453, pp. 524-528.
Park, I. H. et al. "Reprogramming of human somatic cells to pluripotency with defined factors". Nature 451, 141-146, (2008).
Laflamme, M.A. et al. "Cardiomyocytes derived from human embryonic stem cells in pro-survival factors enhance function of infarcted rat hearts". Nature biotechnology 25, 1015-1024 (2007).
Kennedy, M. et al "Development of the hemangioblast defines the onset of hematopoiesis in human ES cell differentiation cultures". Blood 109, 2679-2687.
Boyett, M. R. et al. "The sinoatrial node, a heterogeneous pacemaker structure". Cardiovascular research 47, 658-687 (2000).
Monfredi, O. et al. "The anatomy and physiology of the sinoatrial node—a contemporary review". Pacing and clinical electrophysiology: PACE 33, 1392-1406, doi:10.1111/j.1540-8159.2010.02838.x (2010).
Nof, E. et al. "Genetics and Sinus Node Dysfunction". Journal of atrial fibrillation 1, 328-336 (2009).
Lau, D. et al.. "Sinus node revisited". Current opinion in cardiology 26, 55-59, doi:10.1097/HCO.0b013e32834138f4 (2011).
He, J. Q. et al. "Human embryonic stem cells develop into multiple types of cardiac myocytes: action potential characterization". Circulation research 93, 32-39, doi:10.1161/01.RES.0000080317.92718. 99 (2003).
Ma, J. et al. "High purity human-induced pluripotent stem cell-derived cardiomyocytes: electrophysiological properties of action potentials and ionic currents". American journal of physiology. Heart and circulatory physiology 301, H2006-2017, doi:10.1152/ajpheart.00694.2011 (2011).
Elliott, D. A. et al. "NKX2-5(eGFP/w) hESCs for isolation of human cardiac progenitors and cardiomyocytes". Nature methods 8, 1037-1040, doi:10.1038/nmeth.1740 (2011).
Dubois, N. C. et al. "SIRPA is a specific cell-surface marker for isolating cardiomyocytes derived from human pluripotent stem cells". Nature biotechnology 29, 1011-1018, doi:10.1038/nbt.2005 (2011).
Okada, Y. & SpringerLink (Online service). In Springer Protocols Handbooks, (Springer Japan, Tokyo, 2012) book.
Christoffels, et al. F. "Development of the pacemaker tissues of the heart". Circulation research 106, 240-254, doi:10.1161/CIRCRESAHA. 109.205419 (2010).
Mommersteeg, M. T. et al. "The sinus venosus progenitors separate and diversify from the first and second heart fields early in development". Cardiovascular research 87, 92-101, doi:10.1093/cvr/cvq033 (2010).
Sizarov, A. et al. "Molecular analysis of patterning of conduction tissues in the developing human heart". Circulation. Arrhythmia and electrophysiology 4, 532-542, doi:10.1161/CIRCEP.111.963421 (2011).
Christoffels, V. M. et al. "Formation of the venous pole of the heart from an NKX2-5-negative precursor population requires Tbx18". Circulation research 98, 1555-1563, doi:10.1161/01.RES.0000227571. 84189.65 (2006).
Christoffels, V. M. et al. "Development of the cardiac conduction system: why are some regions of the heart more arrhythmogenic than others?" Circulation. Arrhythmia and electrophysiology 2, 195-207, doi:10.1161/CIRCEP.108.829341 (2009).
Horsthuis, T. et al. "Gene expression profiling of the forming atrioventricular node using a novel tbx3-based node-specific transgenic reporter". Circulation research 105, 61-69, doi:10.1161/CIRCRESAHA.108.192443 (2009).
Witty, A. D. et al. "Generation of the epicardial lineage from human pluripotent stem cells". Nature biotechnology, 32(10):1026-1035 (2014) doi:10.1038/nbt.3002 (2014).
Xavier-Neto, J. et al. "A retinoic acid-inducible transgenic marker of sino-atrial development in the mouse heart". Development 126, 2677-2687 (1999).
Rosenthal, N. et al. "From the bottom of the heart: anteroposterior decisions in cardiac muscle differentiation". Current opinion in cell biology 12, 742-746 (2000).
Pildner von Steinburg, S. et al. "What is the "normal" fetal heart rate?" PeerJ 1, e82, doi:10.7717/peerj.82 (2013).
Keren-Politansky, A. et al. "Neural ectoderm-secreted FGF initiates the expression of NKX2.5 in cardiac progenitors via a p38 MAPK/CREB pathway". Developmental biology 335, 374-384, doi:10. 1016/j.ydbio.2009.09.012 (2009).
Li, R. A. "Gene- and cell-based bio-artificial pacemaker: what basic and translational lessons have we learned?" Gene therapy 19, 588-595, doi:10.1038/gt.2012.33 (2012).
Hu, Y. F. et al. "Biological pacemaker created by minimally invasive somatic reprogramming in pigs with complete heart block." Science translational medicine 6, 245ra294, doi:10.1126/scitranslmed. 3008681 (2014).

* cited by examiner

A

B

C

VLCM Monolayer before

VLCM Monolayer + VLCM control Aggregate

SEQUENCE LISTING

```
<160> NUMBER OF SEQ ID NOS: 36

<210> SEQ ID NO 1
<211> LENGTH: 23
<212> TYPE: DNA
<213> ORGANISM: Homo Sapiens

<400> SEQUENCE: 1
tgtcccaggt ggcttacaga tga                                             23
```

```
<210> SEQ ID NO 2
<211> LENGTH: 23
<212> TYPE: DNA
<213> ORGANISM: Homo Sapiens

<400> SEQUENCE: 2
ggtgtgccaa agttgccaat aca                                              23

<210> SEQ ID NO 3
<211> LENGTH: 24
<212> TYPE: DNA
<213> ORGANISM: Homo Sapiens

<400> SEQUENCE: 3
ttcaccaaag atctgctcct cgct                                             24

<210> SEQ ID NO 4
<211> LENGTH: 26
<212> TYPE: DNA
<213> ORGANISM: Homo Sapiens

<400> SEQUENCE: 4
ttattactgg tgtggagtgg gtgtgg                                           26

<210> SEQ ID NO 5
<211> LENGTH: 24
<212> TYPE: DNA
<213> ORGANISM: Homo Sapiens

<400> SEQUENCE: 5
gcaggcaatc gctcccatca atta                                             24

<210> SEQ ID NO 6
<211> LENGTH: 24
<212> TYPE: DNA
<213> ORGANISM: Homo Sapiens

<400> SEQUENCE: 6
tgtgtacacc ggtggagatt gtgt                                             24

<210> SEQ ID NO 7
<211> LENGTH: 24
<212> TYPE: DNA
<213> ORGANISM: Homo Sapiens

<400> SEQUENCE: 7
tcttcctcat tgtggagaca cgca                                             24

<210> SEQ ID NO 8
<211> LENGTH: 24
<212> TYPE: DNA
<213> ORGANISM: Homo Sapiens

<400> SEQUENCE: 8
tgaggatctt cgtgaagcgg acaa                                             24

<210> SEQ ID NO 9
<211> LENGTH: 24
<212> TYPE: DNA
<213> ORGANISM: Homo Sapiens

<400> SEQUENCE: 9
ttggactcct gggaacatgg acaa                                             24
```

```
<210> SEQ ID NO 10
<211> LENGTH: 24
<212> TYPE: DNA
<213> ORGANISM: Homo Sapiens

<400> SEQUENCE: 10
atgcttcagg gtatctggcc tctt                                          24

<210> SEQ ID NO 11
<211> LENGTH: 21
<212> TYPE: DNA
<213> ORGANISM: Homo Sapiens

<400> SEQUENCE: 11
gaaggtggag ctgcattggt t                                             21

<210> SEQ ID NO 12
<211> LENGTH: 22
<212> TYPE: DNA
<213> ORGANISM: Homo Sapiens

<400> SEQUENCE: 12
taaaccagct acaggacagg cc                                            22

<210> SEQ ID NO 13
<211> LENGTH: 24
<212> TYPE: DNA
<213> ORGANISM: Homo Sapiens

<400> SEQUENCE: 13
tcatcaagat gtcccagccc aaga                                          24

<210> SEQ ID NO 14
<211> LENGTH: 24
<212> TYPE: DNA
<213> ORGANISM: Homo Sapiens

<400> SEQUENCE: 14
cacccggaac ataagcgtga gttt                                          24

<210> SEQ ID NO 15
<211> LENGTH: 20
<212> TYPE: DNA
<213> ORGANISM: Homo Sapiens

<400> SEQUENCE: 15
agcccaagtg acaagggaca                                               20

<210> SEQ ID NO 16
<211> LENGTH: 21
<212> TYPE: DNA
<213> ORGANISM: Homo Sapiens

<400> SEQUENCE: 16
aaggaaccac ttcgaaggtg c                                             21

<210> SEQ ID NO 17
<211> LENGTH: 24
<212> TYPE: DNA
<213> ORGANISM: Homo Sapiens

<400> SEQUENCE: 17
gcgcaagttc cgtcagaaac agta                                          24
```

<210> SEQ ID NO 18
<211> LENGTH: 24
<212> TYPE: DNA
<213> ORGANISM: Homo Sapiens

<400> SEQUENCE: 18
tttgacctgg gtctctgtga ggtt				24

<210> SEQ ID NO 19
<211> LENGTH: 21
<212> TYPE: DNA
<213> ORGANISM: Homo Sapiens

<400> SEQUENCE: 19
tgtccctacc ttgtctgtta g					21

<210> SEQ ID NO 20
<211> LENGTH: 21
<212> TYPE: DNA
<213> ORGANISM: Homo Sapiens

<400> SEQUENCE: 20
attggaacat ggcctctgga t					21

<210> SEQ ID NO 21
<211> LENGTH: 24
<212> TYPE: DNA
<213> ORGANISM: Homo Sapiens

<400> SEQUENCE: 21
tttgcattca ctcctgcgga gacc				24

<210> SEQ ID NO 22
<211> LENGTH: 23
<212> TYPE: DNA
<213> ORGANISM: Homo Sapiens

<400> SEQUENCE: 22
actcattgca cgctgcataa tcg				23

<210> SEQ ID NO 23
<211> LENGTH: 24
<212> TYPE: DNA
<213> ORGANISM: Homo Sapiens

<400> SEQUENCE: 23
tgctgctctt cctcgtcatg ttca				24

<210> SEQ ID NO 24
<211> LENGTH: 24
<212> TYPE: DNA
<213> ORGANISM: Homo Sapiens

<400> SEQUENCE: 24
tgttggcgaa ggtctggaag ttga				24

<210> SEQ ID NO 25
<211> LENGTH: 24
<212> TYPE: DNA
<213> ORGANISM: Homo Sapiens

<400> SEQUENCE: 25
atcgcaaaga ggatgcgaaa ggga                                          24

<210> SEQ ID NO 26
<211> LENGTH: 24
<212> TYPE: DNA
<213> ORGANISM: Homo Sapiens

<400> SEQUENCE: 26
ttccagggtg aaattggtcc gact                                          24

<210> SEQ ID NO 27
<211> LENGTH: 21
<212> TYPE: DNA
<213> ORGANISM: Homo Sapiens

<400> SEQUENCE: 27
tgagttgctc ataccgtgct g                                             21

<210> SEQ ID NO 28
<211> LENGTH: 23
<212> TYPE: DNA
<213> ORGANISM: Homo Sapiens

<400> SEQUENCE: 28
ccctcaaacc aacttgtcaa cag                                           23

<210> SEQ ID NO 29
<211> LENGTH: 24
<212> TYPE: DNA
<213> ORGANISM: Homo Sapiens

<400> SEQUENCE: 29
aacgcatgta catccaccca gaca                                          24

<210> SEQ ID NO 30
<211> LENGTH: 24
<212> TYPE: DNA
<213> ORGANISM: Homo Sapiens

<400> SEQUENCE: 30
ttgttggtca gcttcagctt gtgg                                          24

<210> SEQ ID NO 31
<211> LENGTH: 24
<212> TYPE: DNA
<213> ORGANISM: Homo Sapiens

<400> SEQUENCE: 31
ttgaagacca tggagcccga agaa                                          24

<210> SEQ ID NO 32
<211> LENGTH: 24
<212> TYPE: DNA
<213> ORGANISM: Homo Sapiens

<400> SEQUENCE: 32
cccgcttgtg aaactgatcc caaa                                          24

<210> SEQ ID NO 33
<211> LENGTH: 24
<212> TYPE: DNA
<213> ORGANISM: Homo Sapiens

<400> SEQUENCE: 33

```
acaaagtgaa ggtgacgggc ctta                                          24

<210> SEQ ID NO 34
<211> LENGTH: 24
<212> TYPE: DNA
<213> ORGANISM: Homo Sapiens

<400> SEQUENCE: 34
atctgtgatc gtcggcaggt acaa                                          24

<210> SEQ ID NO 35
<211> LENGTH: 24
<212> TYPE: DNA
<213> ORGANISM: Homo Sapiens

<400> SEQUENCE: 35
ttaaccttgt ccgtctgcct gagt                                          24

<210> SEQ ID NO 36
<211> LENGTH: 24
<212> TYPE: DNA
<213> ORGANISM: Homo Sapiens

<400> SEQUENCE: 36
gtaatgggct ttggcctttg cact                                          24
```

METHODS FOR MAKING AND USING SINOATRIAL NODE-LIKE PACEMAKER CARDIOMYOCYTES AND VENTRICULAR-LIKE CARDIOMYOCYTES

RELATED APPLICATIONS

This is a Patent Cooperation Treaty Application which claims the benefit of 35 U.S.C. § 119 based on the priority of U.S. Provisional Patent Application No. 62/117,107, filed Feb. 17, 2015 which is incorporated herein by reference in its entirety.

INCORPORATION OF SEQUENCE LISTING

A computer readable form of the Sequence Listing "P47907PC00 Sequence Listing_ST25.txt" (5,578 bytes), submitted via EFS-WEB and created on Feb. 17, 2016, is herein incorporated by reference.

FIELD

The disclosure provides methods for producing and compositions comprising sinoatrial node-like pacemaker cardiomyocytes (SANLCM) and ventricular-like cardiomyocytes (VLCM) from human pluripotent stem cells (hPSC).

BACKGROUND

The sinoatrial node (SAN) is the primary pacemaker of the heart and functions to establish the heart rate throughout life[1,2]. Failure of SAN function due to congenital disease or aging results in bradycardia, which eventually leads to circulatory collapse. The standard treatment for SAN failure patients is implantation of an electronic pacemaker that has disadvantages including lack of hormonal responsiveness and risk of infections due to electronic leads[3,4]. Biological pacemakers derived from human pluripotent stem cells (hPSCs) could represent a promising alternative since advances in the stem cell field now allow efficient production of hPSC-derived cardiomyocytes (90%)[5-7]. The cardiomyocyte population consists of a mixture of ventricular, atrial and pacemaker cells.[8,9] However, there are currently only limited strategies to specifically generate and isolate each of these cardiomyocyte subtypes.

In Zhu et al.[23], the progenitor cells having nodal phenotype produced from hPSCs were increased by inhibition of NRG-1β/ErbB signaling. Pacemaker cells were selected from hPSC-derived cardiomyocyte populations using a GATA-6 promoter/enhancer eGFP reporter. The type of nodal cells was not specified. Secondary atrioventricular (AVN) cells can be identified with a GATA-6 reporter in the mouse heart, as shown in Davis et al.[24]

In Kehat et al.[30], cardiomyocyte cell grafts were generated from hPSCs in vitro using an embryoid body differentiating system and were transplanted into hearts of swine with atrioventricular block without selection for pacemaker cells. Only in 6 out of 13 animals a stable ectopic rhythm activated by the human transplant could be seen.

In Ionta et al.[31], it was reported that overexpression of SHOX2 by transduction with an adenoviral vector expressing human SHOX2 during mouse ESC differentiation upregulated the pacemaker gene program, resulting in enhanced automaticity in vitro and induced biological pacing upon transplantation in a rat.

SUMMARY

An aspect includes a method of producing a population of cardiomyocytes from human pluripotent stem cells (hPSCs), the steps comprising:
a. incubating the hPSCs in an embryoid body medium comprising a BMP component, optionally BMP4, optionally further comprising a Rho-associated protein kinase (ROCK) inhibitor, for a period of time to generate embryoid bodies;
b. incubating the embryoid bodies in a mesoderm induction medium comprising a BMP component, optionally BMP4, and an activin component, optionally Activin A, and optionally a FGF component, optionally bFGF, for a period of time to generate cardiovascular mesoderm cells;
c. incubating the cardiovascular mesoderm cells:
  i.
    1. in a cardiac induction medium comprising a BMP component, optionally BMP4, above a selected amount, and retinoic acid (RA), and optionally one or more of a FGF inhibitor, a WNT inhibitor, optionally IWP2, VEGF and an activin/nodal inhibitor, optionally SB-431542; for a period of time to generate cardiovascular progenitor cells that express TBX18 wherein the cardiovascular mesoderm cells are preferably incubated with the FGF inhibitor and which FGF inhibitor is provided for all or part of a cardiac induction phase; and
    2. incubating the cardiovascular progenitor cells in a basic medium comprising VEGF for a period of time to generate a population of cardiomyocytes enriched for SANLCMs; or
  ii.
    1. in a cardiac induction medium comprising one or more of a WNT inhibitor, optionally IWP2, and VEGF; and optionally a FGF component and/or an activin/nodal inhibitor, optionally SB-431542; for a period of time to generate cardiovascular progenitor cells that express NKX2-5 and
    2. incubating the cardiovascular progenitor cells in a basic medium comprising VEGF for a period of time to generate a population of cardiomyocytes that are enriched for NKX2-5$^{pos}$ cTNT$^{pos}$ cells and substantially devoid of SANLCMs; and
d. optionally isolating the population of cardiomyocytes using a cardiomyocyte-specific surface marker, optionally wherein the marker is signal-regulatory protein alpha (SIRPA), and thymocyte differentiation antigen 1 (THY-1/CD90) optionally wherein the isolated population is SIRPA$^{pos}$ CD90$^{neg}$.

In an embodiment, the mesoderm induction medium comprises BMP4 at a concentration of about 1 ng/mL, about 2 ng/mL, about 3 ng/mL, about 4 ng/mL, about 5 ng/mL, about 8 ng/mL, about 10 ng/mL, or up to or about 20 ng/ml optionally about 3 ng/mL, and/or Activin A at a concentration of up to or about 1 ng/mL, about 2 ng/mL, about 3 ng/mL, about 5 ng/mL, about 8 ng/mL, about 10 ng/mL, or up to about 20 ng/mL optionally about 2 ng/mL, preferably wherein the mesoderm induction medium comprises BMP4 at a concentration of about 3 ng/mL and Activin A at a concentration of about 2 ng/mL.

In another embodiment, the cardiovascular mesoderm cells are incubated with BMP4 for about 1 day to about 4 days, optionally 2 days or 3 days, at a concentration of about 0.5 ng/mL, about 1.0 ng/mL, about 1.5 ng/mL, about 2.0 ng/mL, about 2.5 ng/mL, about 3.0 ng/mL, about 5.0 ng/mL, about 10.0 ng/mL, about 20.0 ng/mL, or about 40.0 ng/mL, or about 80.0 ng/mL, optionally about 2.5 ng/mL, and with RA for about 1 day to about 2 days, optionally 1 day, at a concentration of about 20 ng/mL, about 50 ng/mL, about 100 ng/mL, about 150 ng/mL, about 200 ng/mL, about 300 ng/mL, about 400 ng/mL, about 500 ng/mL, or about 1000 ng/mL, optionally about 150 ng/mL. An aspect includes a method of producing a population of cardiomyocytes enriched for sinoatrial node-like pacemaker cardiomyocytes (SANLCM) from human pluripotent stem cells (hPSCs), the steps comprising:

a. incubating the hPSCs in an embryoid body medium comprising a BMP component, optionally BMP4, optionally further comprising a Rho-associated protein kinase (ROCK) inhibitor, for a period of time to generate embryoid bodies;

b. incubating the embryoid bodies in a mesoderm induction medium comprising a BMP component, optionally BMP4, and an activin component, optionally Activin A and optionally a FGF component, optionally bFGF, for a period of time to generate cardiovascular mesoderm cells;

c.
  i. incubating the cardiovascular mesoderm cells in a cardiac induction medium comprising a BMP component, optionally BMP4, above a selected amount, and retinoic acid (RA), and optionally one or more of a FGF inhibitor, a WNT inhibitor, optionally IWP2, VEGF and an activin/nodal inhibitor, optionally SB-431542; for a period of time to generate cardiovascular progenitor cells that express TBX18; wherein the cardiovascular mesoderm cells are preferably incubated with the FGF inhibitor and which FGF inhibitor is provided for all or part of the cardiac induction phase; and
  ii. incubating the cardiovascular progenitor cells in a basic medium comprising VEGF for a period of time to generate a population of cardiomyocytes enriched for SANLCMs; and d. optionally isolating the population of cardiomyocytes enriched for SANLCMs using a cardiomyocyte-specific surface marker, optionally wherein the marker is signal-regulatory protein alpha (SIRPA), and thymocyte differentiation antigen 1 (THY-1/CD90) optionally wherein the isolated population is SIRPA$^{pos}$ CD90$^{neg}$.

In embodiments for producing a population of cardiomyocytes enriched for SANLCM, the cardiovascular mesoderm cells are preferably incubated in a cardiac induction medium comprising BMP4 above a selected amount, RA, and a FGF inhibitor.

In an embodiment, the FGF inhibitor is selected from PD 173074 (Torcis), SU 5402 (Torcis), and any other FGF receptor inhibitor or FGF signaling inhibitor.

In an embodiment, the cardiovascular mesoderm cells are incubated with the FGF inhibitor for at about 2 to about 7 days, optionally about 2 days, about 3 days, about 4 days or about 5 days.

An aspect includes a method of producing a population of cardiomyocytes substantially devoid of SANLCM from human pluripotent stem cells (hPSCs), the steps comprising:

a. incubating the hPSCs in an embryoid body medium comprising a BMP component, optionally BMP4, optionally further comprising a Rho-associated protein kinase (ROCK) inhibitor, for a period of time to generate embryoid bodies;

b. incubating the embryoid bodies in a mesoderm induction medium comprising a BMP component, optionally BMP4, and an activin component, optionally Activin A and optionally a FGF component, optionally bFGF, for a period of time to generate cardiovascular mesoderm cells;

c.
  i. incubating the cardiovascular mesoderm cells in a cardiac induction medium comprising one or more of a WNT inhibitor, optionally IWP2, and VEGF; and optionally a FGF component and/or an activin/nodal inhibitor, optionally SB-431542; for a period of time to generate cardiovascular progenitor cells that express NKX2-5; and
  ii. incubating the cardiovascular progenitor cells in a basic medium comprising VEGF for a period of time to generate a population of cardiomyocytes that are enriched for NKX2-5$^{pos}$ cTNT$^{pos}$ cells and substantially devoid of SANLCMs; and d. optionally isolating the population of cardiomyocytes using a cardiomyocyte-specific surface marker, optionally wherein the marker is signal-regulatory protein alpha (SIRPA) and thymocyte differentiation antigen 1 (THY-1/CD90) optionally wherein the isolated population is SIRPA$^{pos}$ CD90$^{neg}$.

In embodiments directed to obtaining a population of cardiomyocytes substantially devoid of SANLCM, the cardiovascular mesoderm cells are preferably incubated with FGF component, optionally bFGF.

In an embodiment, the cardiovascular mesoderm cells are incubated with the FGF component for at about 2 to about 7 days, optionally about 2 days, about 3 days, about 4 days or about 5 days.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

An embodiment of the present disclosure will now be described in relation to the drawings in which.

DETAILED DESCRIPTION OF THE DISCLOSURE

I. Definitions

Figure 1:
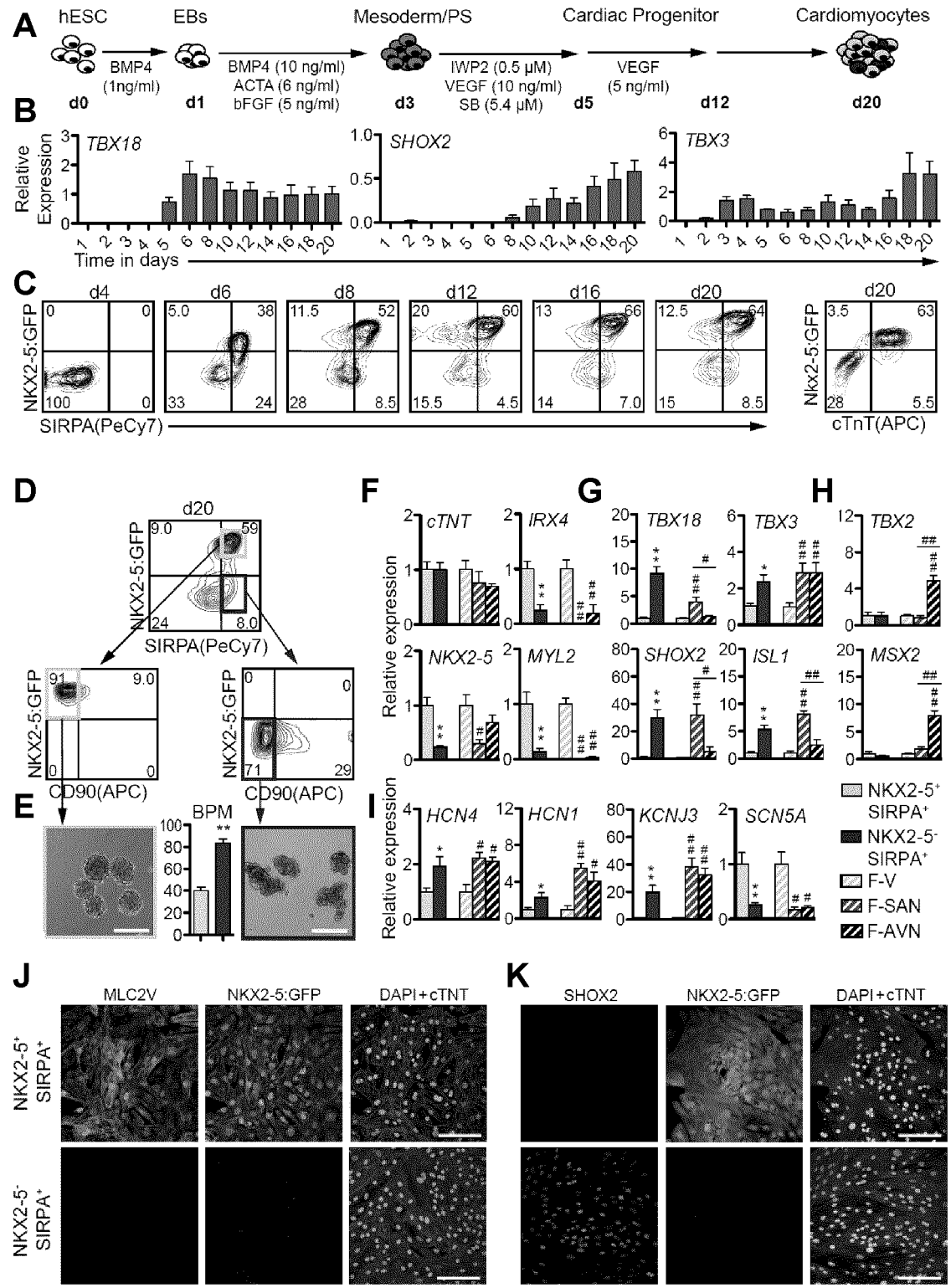
FIG. 1. Enrichment for sinoatrial node pacemaker-like cardiomyocytes by sorting for NKX2-5 negative, SIRPA positive cells. A, Scheme of the developmentally staged protocol used for hESC differentiation into cardiomyocytes. B, Q-PCR analysis of pacemaker markers at different time points during differentiation. C, Representative FACS plots for SIRPA/cTNT and NKX2-5 expression during differentiation using the NKX2-5:GFP hESC line. D, Representative FACS plots of sorting strategy for NKX2-5$^+$SIRPA$^+$CD90$^-$ and NKX2-5$^-$SIRPA$^+$CD90$^-$ populations at day 20 of differentiation. E, Brightfield and GFP channel overlay image of NKX2-5$^+$SIRPA$^+$ and NKX2-5$^-$SIRPA$^+$ sorted populations and quantification of beating rates (n=30). Scale bars represent 200 μm. F-I, Q-PCR analysis of: pan-cardiomyocyte and ventricular marker (f), SAN pacemaker marker (G), AVN pacemaker marker (H) and cardiac ion channels (i), in NKX2-5$^+$SIRPA$^+$ and NKX2-5$^-$SIRPA$^+$ sorted cells. Fetal tissue was used as expression reference. Expression relative to housekeeping gene TBP, normalized to NKX2-5$^+$SIRPA$^+$ for hESC-derived cell populations and F-V for fetal tissue samples. T-test: *P<0.05, **P<0.01 vs NKX2-5$^+$SIRPA$^+$ cells, #P<0.05, ##P<0.01 vs F-V or indicated sample (n=5). Error bars show s.e.m. J,K, Immunostaining for ventricular contractile apparatus marker MLC2V (j) and pacemaker transcription factor SHOX2 (K) in NKX2-5$^+$SIRPA$^+$ and NKX2-5$^-$SIRPA$^+$ sorted cells from day 20 cultures. Cells were counterstained with cTNT to mark cardiomyocytes and DAPI to mark cell nuclei. Scale bars represent 100 µm. BPM, beats per minute; d, day; PS, primitive streak; F-V, fetal ventricle; F-SAN, fetal sinoatrial node; F-AVN, fetal atrioventricular node.

The term "sinoatrial node-like cardiomyocytes" or "SAN-LCM" as used herein refers to a subtype of cardiomyocytes that express sinoatrial nodal (SAN) cell specific markers TBX18, TBX3, SHOX2 and ISL1 and which have pacemaker activity. Like SAN cells, SANLCMs express low levels of NKX2-5 and have faster beating rates (e.g. beats per minute) than other cardiomyocyte subtypes such as ventricular-like cardiomyocytes.

The term "ventricular-like cardiomyocytes" or "VLCM" as used herein refers to a subtype of cardiomyocytes expressing ventricular specific markers MYL2 and IRX4, as well as elevated levels of NKX2-5.

The term "atrioventricular (AVN) cardiomyocytes" as used herein is a subtype of cardiomyocytes that express TBX2 and MSX2 and can act as a secondary pacemaker. AVN cardiomyocytes are distinguishable from SANLCMs which do not express TBX2 and/or MSX2

The term "cardiomyocyte" as used herein is a cardiac lineage cell that expresses cTNT and SIRPA.

The term "NKX2-5" as used herein refers to the cardiac homeobox protein NKX2-5 encoded in humans by the NKX2-5 gene. The gene is involved in the cardiac differentiation and is expressed in cardiomyocyte subtypes such as ventricular cardiomyocytes. Expression of NKX2-5 can be measured using for example an antibody specific to NKX2-5 or for example by using a NKX2-5 reporter construct.

The term "NKX2-5 negative cell" as used herein means a cell with no detectable NKX2-5 protein expression and/or a cell with detectable expression below a selected threshold when analyzed for example by flow cytometry. For example, NKX2-5 expression can be detected using a reporter assay such as a GFP reporter assay described herein or using an intracellular antibody for NKX2-5 protein. When using an intracellular antibody, an aliquot of cells to be tested are fixed, and stained as described in FIG. 12F and a method described in the Examples section.

The threshold for example can be based on a mixed population of cardiomyocyte lineage cells prepared according to a method described herein wherein the threshold is selected based on an expression level that separates the mixed population into two groups. The threshold can also be based on comparison to a control. For example, the control when staining cells for NKX2-5 expression can be undifferentiated hPSCs or a fibroblast cell line which are cells known to not express NKX2-5. As used herein, "NKX2-5 negative cell" also means a cell comprising a NKX2-5 reporter, for example a NKX2-5:GFP reporter, with no detectable expression of the fluorescent protein when analyzed, for example by flow cytometry or expression below a threshold or relative to a control.—For example, in the case of an NKX2-5 reporter line a good negative control would be to use cardiomyocytes that were differentiated from a hPSC line that does not carry the reporter. In addition, an internal control can be used. For example, cells can be co-stained with an antibody for cTNT. In such case cTNT-neg non-cardiomyocytes will not express NKX2-5 and can be used as an internal negative control.

The term "BMP component" as used herein means any molecule optionally any BMP or growth and differentiation factor (GDF) that activates the receptor for BMP4, including for example BMP4 and BMP2.

The term "BMP4" (for example Gene ID: 652) as used herein refers to Bone Morphogenetic Protein 4, for example human BMP4, as well as active conjugates and fragments thereof, that can for example activate BMP4 receptor signlaing.

The term "activin component" as used herein means one or more components, or a composition comprising said component(s) that activates nodal signal transduction, optionally which has Activin A activity such as Activin A and/or nodal.

The term "activin" or "ActA" as used herein refers to "Activin A", (e.g. Gene ID: 3624), for example human activinA, as well as active conjugates and fragments thereof, that can activate nodal signal transduction.

The term "activin/nodal inhibitor" and/or "activin/nodal/TGF-βR inhibitor" as used herein means any molecule that inhibits signal of the activin/nodal pathway and particularly any molecule that inhibits receptors ALK4, ALK7 and/or TGF-βRI, including but not limited to SB431542 (Sigma Aldrich) A83-01 (Tocris, 2929), D 4476, GW 788388, LY 364947, RepSox, SB 505124, SB 525334 (Sigma Aldrich), and SD 208.

The term "wnt inhibitor" as used herein means any agent, including any compound and/or protein that inhibits wnt signaling, including but not limited to wnt antagonists that bind either to the Wnt ligand itself, or to Wnt receptors, such as Dickkopf (Dkk) proteins, Wnt Inhibitory Factor-1 (WIF-1), and secreted Frizzled-Related Proteins (sFRPs), as well as wnt inverse agonists (e.g. an agent that binds to the same receptor as an agonist but induces a pharmacological response opposite to that of an agonist). Examples of Wnt inhibitors include XAV939, IWP 2, an inhibitor of wnt processing, and iCRT14, which is a potent inhibitor of β-catenin-responsive transcription (CRT), both of which are available from Tocris Bioscience, as well as combinations thereof.

The term "FGF component" as used herein means a molecule such as a cytokine, including for example FGF, or a small molecule, that activates a FGF signalling pathway, e.g. binds and activates a FGF receptor. The term "FGF" as used herein refers to any fibroblast growth factor, for example human FGF1 (Gene ID: 2246), FGF2 (also known as bFGF; Gene ID: 2247), FGF3 (Gene ID: 2248), FGF4 (Gene ID: 2249), FGF5 (Gene ID: 2250), FGF6 (Gene ID: 2251), FGF7 (Gene ID: 2252), FGF8 (Gene ID: 2253), FGF9 (Gene ID: 2254) and FGF10 (Gene ID: 2255) optionally including active conjugates and fragments thereof, including naturally occuring active conjugates and fragments. In certain embodiments, FGF is bFGF, FGF10, FGF4 and/or FGF2.

The term "retinoic acid" or "RA" includes vitamin A and metabolites of vitamin A that mediate the function of vitamin A, and includes for example all-trans RA (e.g. Sigma R2625), 9-cis RA (e.g. Sigma R4643), and retinol (e.g. Sigma R7632) as well as RA analogs (e.g. RARβ agonists), such as AM580, a selective RARα agonist (Tocris 0760), AC55649, a selective RARβ agonist (Tocris 2436), and CD437, a selective RARγ agonist (Tocris 1549).

The term "FGF inhibitor" as used herein means any FGF receptor inhibitor (FGFR 1,2,3,4) or FGF signaling inhibitor (i.e. downstream p38 MAPK inhibitor), including but not limited to PD 173074 (Tocris) and SU 5402 (Torcis) and p38 MAPK inhibitor SB203580 (Tocris).

The term "SIRPA" as used herein refers to the signal-regulatory protein alpha (SIRPA) pan-cardiomyocyte cell surface marker, including for example human SIRPA (e.g. GENE ID: 140885).

The term "embryoid body medium" as used herein is a culture medium that supports formation of aggregates (e.g. floating aggregates) from embryonic/pluripotent stem cells and comprising a minimal media such as StemPro 34 (ThermoFisher), MesoFate™ (Stemgent), RPMI (ThermoFisher and other companies), HES-media (DMEM/F12 with KnockOut Serum Replacement, ThermoFisher and other companies) and for example a BMP component, optionally BMP4, and further optionally comprising a Rho-associated protein kinase (ROCK) inhibitor. An example of an embryoid body medium is provided in Example 1.

The term "embryoid body aggregation phase" as used herein means the time period non-aggregated hPSCs are cultured for example with an embryoid body medium described herein and are treated with BMP component and as well as optionally ROCK inhibitor and/or other components that result in embryoid bodies (i.e. aggregates of embryonic/pluripotent stem cells that can be differentiated). The component treatments can be simultaneous, overlapping or distinct. For example, a first component can be comprised in the medium and a second component can be added to the medium during the embryoid body aggregation phase.

The term "mesoderm induction medium" as used herein is a culture medium that supports the formation of cardiovascular mesoderm cells and comprises a minimal media such as StemPro 34 (ThermoFisher), MesoFate™ (Stemgent), RPMI (ThermoFisher and other companies), and for example a BMP component, optionally BMP4, above a selected amount, and an activin component, optionally Activin A and optionally comprising a FGF component, optionally bFGF. An example of a mesoderm induction medium is provided in Example 1.

The term "mesoderm induction phase" as used herein means the time period mesoderm cells are cultured with mesoderm induction medium and are treated with BMP component and an activin component as well as optionally FGF component and/or other components that result in cardiovascular mesoderm cells. The component treatments can be simultaneous, overlapping or distinct. For example, a first component can be comprised in the medium and a second component can be added to the medium during the mesoderm induction phase.

The term "cardiac induction medium" as used herein is a culture medium that supports cardiac progenitor cells such as StemPro-34 minimal media comprising for example a WNT inhibitor, optionally IWP2, VEGF and/or an optionally activin/nodal inhibitor, optionally SB-431542. Depending on the desired cell type, the cardiac induction medium may also comprise a BMP component, retinoic acid, an FGF inhibitor or a FGF component. An example of a cardiac induction medium is provided in Example 1. An example of a cardiac induction medium (also referred to as standard cardiac induction media) is StemPro-34 minimal media containing 0.5 µM IWP2, 10 ng/ml VEGF, and optionally 5.4 µM SB-431542. Other minimal media that can be used include MesoFate™ (Stemgent) and RPMI (ThermoFisher and other companies).

The term "cardiac induction phase" as used herein means the time period cardiac progenitor cells are cultured with cardiac induction medium and are treated for example with BMP component and RA as well as optionally an FGF inhibitor or FGF component and/or other components that result in cardiovascular progenitor cells. The treatments can be simultaneous, overlapping or distinct. For example, a first component can be comprised in the medium and a second component can be added to the medium during the cardiac induction phase.

The term "basic medium" as used here is a culture medium that supports growth of cardiovascular progenitor cells and cardiomyocytes comprising a minimal media such as StemPro 34 (ThermoFisher), MesoFate™ (Stemgent), RPMI (ThermoFisher and other companies), and for example VEGF. An example of a basic medium is provided in Example 1.

The term "basic phase" as used herein means the time period cardiovascular progenitor cells are cultured with basic medium and are treated with VEGF and/or other components that result in cardiomyocytes. The treatments can be simultaneous, overlapping or distinct.

The term "incubating" as used herein includes any in vitro method of maintaining and/or propagating a population of cells, including monolayer, bead, flask, or 3D cultures, optionally where ambient conditions are controlled as in an incubator and optionally involving passaging of cells. Steps that involve incubating the cells with more or more components, the components can be added simultaneously, at different times, for overlapping periods or for distinct periods. A factor can be added to the medium after the cells have started incubating in for example an induction medium or the factor can be added to the medium before the medium is added to the cells. Further, cells may be washed between incubations, for example to reduce the level of a component from a previous incubation.

The term "culturing" as used herein means any in vitro method of maintaining and propagating a population of cells at least through one cell division, including monolayer, bead, flask, or 3D cultures, optionally where ambient conditions are controlled as in an incubator.

The term "substantially devoid of SANLCMs" as used herein means a population of cells comprising less than 30%, less than 25%, less than 20%, or less than 15%, less than 10%, or less than 5% SANLCMs. In an embodiment, a population substantially devoid of SANLCMs is enriched for VLCMs.

The term "enriched for SANLCMs" as used herein means a population of cells comprising at least 30%, at least 40%, at least 50%, at least 60%, or at least 70% up to 100% SANLCMs, for example in a day 20 culture using a method described in the Examples. The population "enriched for SANLCMs" can be further enriched or purified by isolating or purifying cells using for example SIRPA$^{pos}$ or SIRPA$^{pos}$ NKX2-5$^{neg}$ based cell sorting. Isolated and/or purified SAN-LCMs based on SIRPA$^{pos}$ CD90$^{neg}$ can result in for example a population of cardiomyocytes wherein at least 60%, at least 70%, at least 80% or at least 90% up to 100% are NKX2-5$^{neg}$ SANLCM.

The term "subject" as used herein includes all members of the animal kingdom including mammals, and suitably refers to humans.

The terms "treat", "treating", "treatment", etc., as applied to a cell, include subjecting the cell to any kind of process or condition or performing any kind of manipulation or procedure on the cell. As applied to a subject, the terms refer to providing medical or surgical attention, care, or management to an individual.

The term "treatment" as used herein as applied to a subject, refers to an approach aimed at obtaining beneficial or desired results, including clinical results and includes medical procedures and applications including for example pharmaceutical interventions, surgery, radiotherapy and naturopathic interventions as well as test treatments for treating cancer. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

As used herein, the terms "administering", "introducing" and "transplanting" are used interchangeably in the context of delivering cells into a subject, by a method or route which results in at least partial localization of the introduced cells at a desired site.

The term "medium" as referred to herein is a culture medium for culturing cells containing nutrients that maintain cell viability and support proliferation and optionally differentiation. The medium may contain any of the following in an appropriate combination: salt(s), buffer(s), amino acids, glucose or other sugar(s), antibiotics, serum or serum replacement, and other components such as peptide growth factors, vitamins etc. For example, StemPro can be used as a medium.

The term "pluripotent stem cell" or "PSC" as used herein refers to a cell with the capacity, under different conditions, to differentiate to more than one differentiated cell type, and for example the capacity to differentiate to cell types characteristic of the three germ cell layers, and includes embryonic stem cells and induced pluripotent stem cells. Pluripotent cells are characterized by their ability to differentiate to more than one cell type using, for example, a nude mouse teratoma formation assay. Pluripotency is also evidenced by the expression of embryonic stem (ES) cell markers. As used herein, pluripotent stems can include cell lines and induced pluripotent stem cells (iPSC) and embryonic stem cells (ESC).

In an embodiment, the term "embryonic stem cells" excludes stem cells involving destruction of an embryo such as a human embryo.

As used herein, the terms "iPSC" and "induced pluripotent stem cell" are used interchangeably and refers to a pluripotent stem cell artificially derived (e.g., induced or by complete reversal) from a non-pluripotent cell, typically an adult somatic cell, for example, by inducing expression of one or more genes (including POU4F1/OCT4 (Gene ID; 5460) in combination with, but not restricted to, SOX2 (Gene ID; 6657), KLF4 (Gene ID; 9314), cMYC (Gene ID; 4609), NANOG (Gene ID; 79923), LIN28/LIN28A (Gene ID; 79727)).

The term "embryonic stem cell" is used to refer to the pluripotent stem cells of the inner cell mass of the embryonic blastocyst (see, for example, U.S. Pat. Nos. 5,843,780, 6,200,806). Such cells can also be obtained from the inner cell mass of blastocysts derived from somatic cell nuclear transfer (see, for example, U.S. Pat. Nos. 5,945,577, 5,994, 619, 6,235,970). The distinguishing characteristics of an embryonic stem cell define an embryonic stem cell phenotype. Accordingly, a cell has the phenotype of an embryonic stem cell if it possesses one or more of the unique characteristics of an embryonic stem cell such that that cell can be distinguished from other cells. Exemplary distinguishing embryonic stem cell characteristics include, without limitation, gene expression profile, proliferative capacity, differentiation capacity, karyotype, responsiveness to particular culture conditions, and the like.

The term "pharmaceutically acceptable carrier" as used herein includes essentially chemically inert and nontoxic compositions that do not interfere with the effectiveness of the biological activity of the pharmaceutical composition. Examples of suitable pharmaceutical carriers include, but are not limited to, water, saline solutions, glycerol solutions, ethanol, N-(1(2,3-dioleyloxy)propyl)N,N,N-trimethylammonium chloride (DOTMA), diolesylphosphotidyl-ethanolamine (DOPE), and liposomes. Such compositions should contain a therapeutically effective amount of the compound(s), together with a suitable amount of carrier so as to provide the form for direct administration to the subject.

The term "expression" refers to the cellular processes involved in producing RNA and proteins and as appropriate, secreting proteins, and cell surface expression, including where applicable, but not limited to, for example, transcription, translation, folding, modification and processing. "Expression products" include RNA transcribed from a gene and polypeptides obtained by translation of mRNA transcribed from a gene.

In understanding the scope of the present disclosure, the term "concentration" as used herein means a final concentration of a substance such as for example BMP4, Activin A, retinoic acid in a medium. Unless indicated otherwise, the concentration is based on a weight/volume ratio.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

In understanding the scope of the present disclosure, the term "consisting" and its derivatives, as used herein, are intended to be close ended terms that specify the presence of stated features, elements, components, groups, integers, and/or steps, and also exclude the presence of other unstated features, elements, components, groups, integers and/or steps.

The recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about." Further, it is to be understood that "a," "an," and "the" include plural referents unless the content clearly dictates otherwise. The term "about" means plus or minus 0.1 to 50%, 5-50%, or 10-40%, preferably 10-20%, more preferably 10% or 15%, of the number to which reference is being made.

Further, the definitions and embodiments described in particular sections are intended to be applicable to other embodiments herein described for which they are suitable as would be understood by a person skilled in the art. For example, in the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

II. Methods and Products

Described herein are methods for producing and isolating a population of cells enriched for- or substantially devoid-of SANLCMs. Components and conditions for specifying this cell type as well as markers for monitoring emergence of these cells are described.

An aspect includes a method of producing a population of cardiomyocytes enriched for sinoatrial node-like pacemaker cardiomyocytes (SANLCM) from human pluripotent stem cells (hPSCs), the steps comprising:
   a. incubating cardiovascular mesoderm cells in a cardiac induction medium comprising a BMP component, optionally BMP4, above a selected amount, and retinoic acid (RA), and optionally one or more of a WNT inhibitor, optionally IWP2, VEGF; and an activin/nodal inhibitor, optionally SB-431542; for a period of time to generate cardiovascular progenitor cells that express TBX18;
   b. incubating the cardiovascular progenitor cells in a basic medium comprising VEGF for a period of time to generate a population of cardiomyocytes enriched for SANLCMs; and
   c. optionally isolating the population of cardiomyocytes enriched for SANLCMs using a cardiomyocyte-specific surface marker, optionally wherein the marker is signal-regulatory protein alpha (SIRPA), optionally wherein the isolated population is SIRPA$^{pos}$ CD90$^{neg}$.

Figure 5:
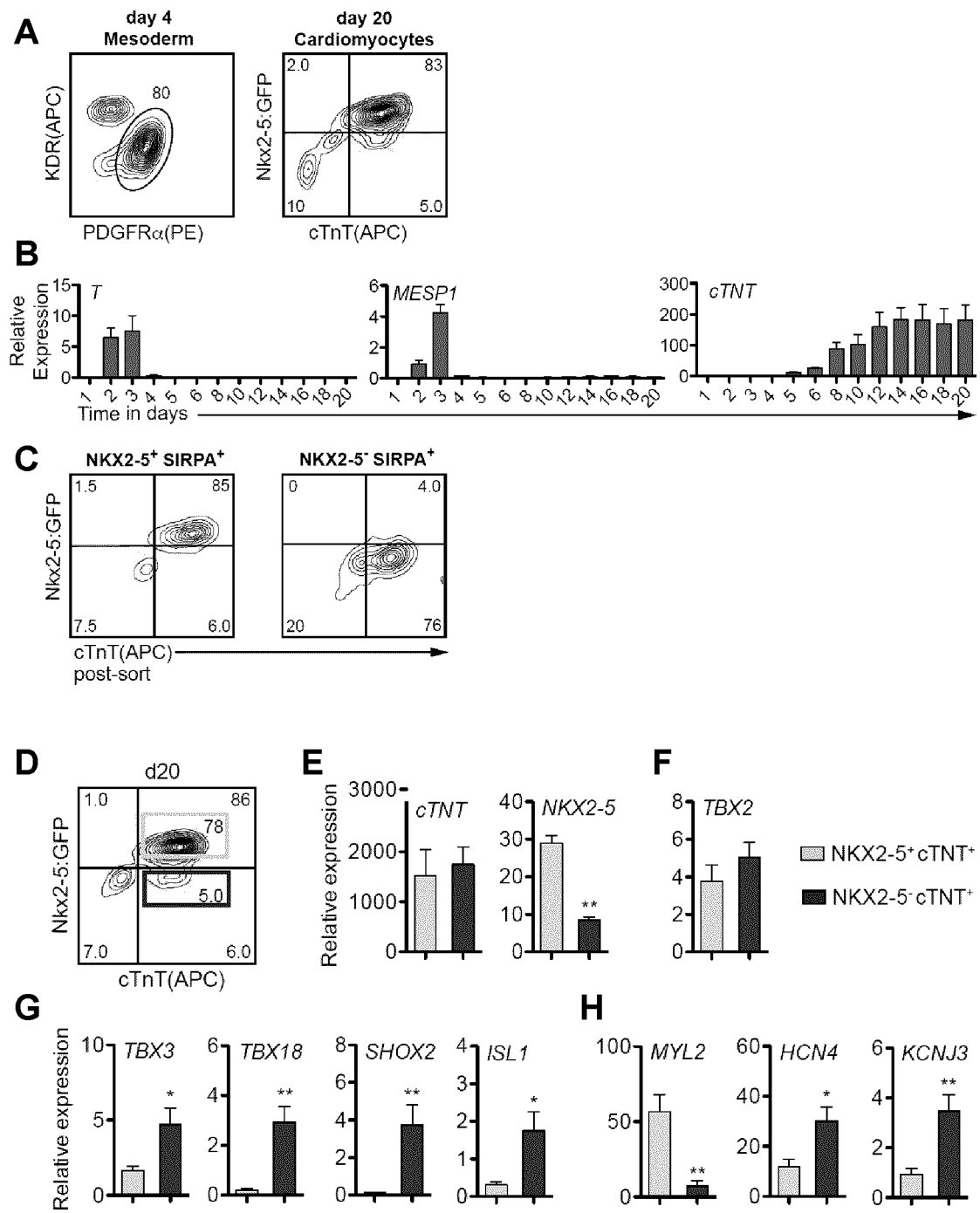
FIG. 5. A, Representative FACS plot for PDGFRα$^+$, KDR$^+$ cardiac mesoderm at day 4 of differentiation and resulting cTNT population at day 20 of differentiation. B, Q-RT-PCR analysis of mesoderm and cardiac markers at different time points during differentiation. C, Representative FACS plot of cTNT analysis in the NKX2-5$^+$SIRPA$^+$ and NKX2-5$^-$ SIRPA$^+$ populations after sort. D, Representative FACS plot of sorting strategy for NKX2-5$^+$cTNT$^+$ and NKX2-5$^-$ cTNT$^+$ cells from PFA fixed day 20 cultures. E-H, Q-PCR analysis of: sorting markers (E), AVN pacemaker marker (F), SAN pacemaker marker (G), ventricular marker and cardiac ion-channels (H), in NKX2-5$^+$cTNT$^+$ and NKX2-5$^-$ cTNT$^+$ sorted cells. Expression relative to housekeeping gene TBP. T-test: *P<0.05, **P<0.01 vs NKX2-5$^+$ cTNT$^+$ cells (n=3). Error bars show s.e.m.

In some embodiments, the starting population is cardiovascular mesoderm cells. Such cells, as shown in FIG. 5a express surface markers PDGRFalpha$^{(high)}$ and KDR$^{(low)}$. In addition, these cells express surface marker CD56. As shown in FIG. 5B, these cells express MESP1 and T(Brachyury) by Q-RT-PCR and can give rise to cTNT$^+$ cardiomyocytes under conditions described herein and for example in Example 1.

Figure 12:
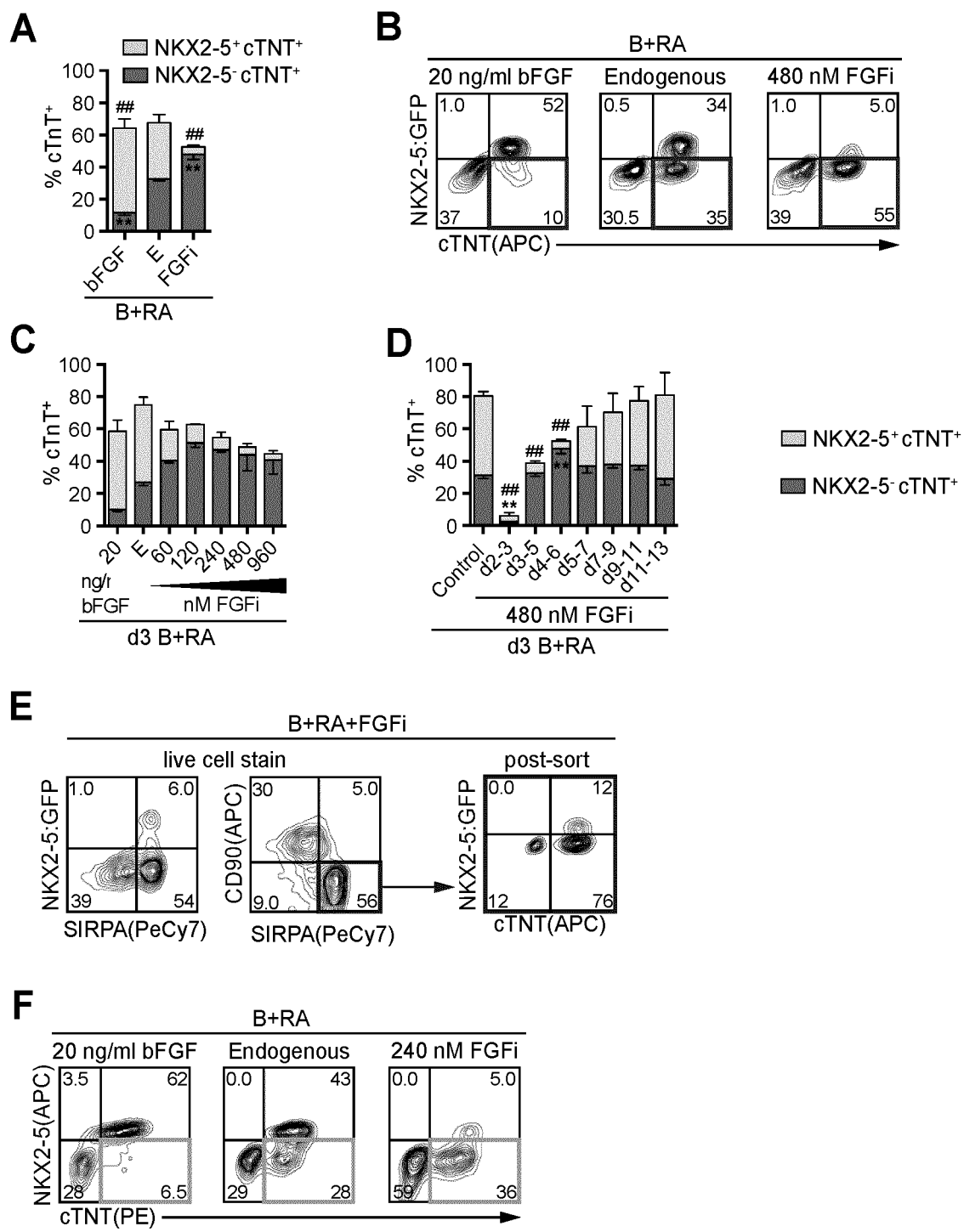
FIG. 12. SANLCM can be isolated from hPSC lines without transgenic NKX2-5:GFP reporter. (A) Flow cytometric analyses of day 20 cultures for the proportion of NKX2-5⁺cTNT⁺ and NKX2-5⁻cTNT⁺ cells after treatment with BMP (2.5 ng/ml) and RA (0.5 µM) from day 3-6 and either bFGF (20 ng/ml) or FGFi (480 nM) from day 4-6. Error bars represent s.e.m. One-way ANOVA followed by Bonferroni's post hoc test: P<0.01 vs NKX2-5⁻cTNT⁺ cells at endogenous (E) bFGF levels, ##P<0.01 vs NKX2-5⁺cTNT⁺ cells at endogenous (E) bFGF levels (n=4). (B) Representative flow cytometric analyses showing the proportion of NKX2-5⁻cTNT⁺ SANLCMs and NKX2-5⁺cTNT⁺ cells in day 20 populations that were treated with BMP(2.5 ng/ml) and RA(0.5 µM) from day 3-6 and either bFGF (20 ng/ml) or no additional bFGF (endogenous) or FGFi (480 nM) from day 4-6. (C) Flow cytometric analyses of day 20 cultures for the proportion of NKX2-5⁺cTNT⁺ and NKX2-5⁻cTNT⁺ cells after treatment with BMP (2.5 ng/ml) and RA (0.5 µM) from day 3-6 and indicated amounts of FGFi from day 4-6. Error bars represent s.e.m. (n=2). (D) Flow cytometric analyses of day 20 cultures for the proportion of NKX2-5⁺cTNT⁺ and NKX2-5⁻cTNT⁺ cells after treatment with BMP (2.5 ng/ml) and RA (0.5 µM) from day 3-5 and FGFi (480 nM) at indicated time points. Error bars represent s.e.m. One-way ANOVA followed by Bonferroni's post hoc test: P<0.01 vs NKX2-5⁻cTNT⁺ cells in untreated Control, ##P<0.01 vs NKX2-5⁺cTNT⁺ cells in untreated Control (n=3). (E) Representative flow cytometric analyses of live cultures showing the proportion of NKX2-5⁻SIRPA⁺ cells and CD90⁻SIRPA⁺ cells in day 20 populations specified with BMP and RA at day 3 and FGFi at day 4. To enrich for SANLCMs cultures were sorted based on SIRPA⁺CD90⁻ expression (highlighted quadrant) and checked for their post-sort purity by NKX2-5:GFP and cTNT flow cytometric analysis on fixed cells. (F) Representative flow cytometric analyses of HES2 hESC-line derived day 20 cultures that were specified with BMP (2.5 ng/ml) and RA (0.5 µM) from day 3-5 and either bFGF (20 ng/ml) or no additional bFGF (endogenous) or FGFi (240 nM) from day 3-5 showing the proportion of NKX2-5⁻ cTNT⁺ SANLCMs and NKX2-5⁺cTNT⁺ cells.

As demonstrated in FIG. 12, addition of FGF inhibitor to cardiovascular mesoderm cells dramatically increases the proportion of SANLCMS when assessed at day 20 of culture.

Accordingly in an embodiment, the cardiovascular mesoderm cells are also treated with FGF inhibitor for all or part of the cardiac induction phase.

In embodiments for producing a population of cardiomyocytes enriched for SANLCM, the cardiovascular mesoderm cells are preferably incubated in a cardiac induction medium comprising BMP4 above a selected amount, RA, a WNT inhibitor, VEGF, an activin/nodal inhibitor, and a FGF inhibitor.

In an embodiment, the FGF inhibitor is selected from PD 173074 (Torcis), SU 5402 (Torcis), and any other FGF receptor inhibitor or FGF signaling inhibitor.

Exemplary concentrations include 60 nM to 5 microMolar for PD173074, 5 microMolar to 10 mM for SU 5402, or 1 microMolar to 1 mM for p38MAPK inhibitor SB203580. Any 1 nanoMolar increment between the stated ranges is also contemplated. For example the concentration of PD173074 can be 61 nM, 62 nM, 63 nM etc In an embodiment, the concentration of PD173074 includes or is selected to be between 60 nM and 5 microMolar, for example, at least or about 0.12 microMolar, at least or about 0.24 microMolar, at least or about 0.5 microMolar, at least or about 0.75 microMoalar, at least or about 1 microMolar, at least or about 2 microMolar, at least or about 3 microMolar, at least or about 4 microMolar or about 5 microMolar. In an embodiment, the concentration of PD173074 is about 240 to about 960 nM.

In an embodiment, the cardiovascular mesoderm cells are incubated with the FGF inhibitor for about 2 to about 7 days, optionally about 2 days, about 3 days, about 4 days or about 5 days.

The FGF inhibitor can be added between about 2.5 days and 5 days of differentiation. The FGF inhibitor is added between about day 2.5 to about day 5 which corresponds to the period when co-expression of PDRGFalpha and CD56 is first detectable by flow cytometry and when T(Brachyury) and MESP1 expression determined by Q-RT PCR reaches its maximum expression. As shown herein, both T(Brachyury) and MESP1 peak expression around day 3 and then decrease—see FIG. 5B).

As demonstrated in FIG. 12, the method can be performed without a NKX2-5 reporter when FGF inhibitor is added to the cardiac induction phase, permitting obtaining cultures that do not contain (or contain few) NKX2-5+ cells. These cultures contain predominantly SANLCM and non-cardiomyocytes. Sorting for SIRPA+CD90– cells allows for purification of SANLCM (as only few NKX2-5+ cells are present in the culture) from the non-cardiomyocytes.

Another aspect includes a method of producing a population of cardiomyocytes substantially devoid of SANLCM from human pluripotent stem cells (hPSCs), the steps comprising:
   a. incubating cardiovascular mesoderm cells in a cardiac induction medium comprising one or more of a WNT inhibitor, optionally IWP2, and VEGF; and optionally a FGF component and/or an activin/nodal inhibitor, optionally SB-431542; for a period of time to generate cardiovascular progenitor cells;
   b. incubating the cardiovascular progenitor cells in a basic medium comprising VEGF for a period of time to generate a population of cardiomyocytes that are enriched for NKX2-5$^{pos}$ cTNT$^{pos}$ and substantially devoid of SANLCMs; and
   c. optionally isolating the population of cardiomyocytes that are NKX2-5$^{pos}$ cTNT$^{pos}$ substantially devoid of SANLCMs using a cardiomyocyte-specific surface marker optionally wherein the marker is signal-regulatory protein alpha (SIRPA), optionally wherein the isolated population is SIRPA$^{pos}$ CD90$^{neg}$.

Addition of an activin/nodal inhibitor during the cardiovascular mesoderm cells for embodiments where a population substantially devoid of SANLCMs are desired, may be optionally used. For example any hESC or hIPSC cell line that has relatively high endogenous levels of activin signaling is preferably treated with an activin/nodal inhibitor such as SB-431542.

In an embodiment, the cardiac induction medium comprises a WNT inhibitor and VEGF. In an embodiment, either a WNT inhibitor or VEGF can be used. As shown herein, inclusion of both components increases the efficiency of generating NKX2-5pos cTNTpos cells. For example, the combination can result in up to 80% of the culture comprising NKX2-5pos cTNTpos cells.

In an embodiment, the FGF component used to treat the cardiac mesoderm cells is bFGF. Other FGF components as described herein can also be used.

In an embodiment, the concentration of bFGF in the cardiac induction medium is from about 0.25-100 ng/ml or any 0.1 ng/ml increment there between, for example about 1 ng/ml, about 10 ng/ml, about 20 ng/ml, about 30 ng/ml, about 40 ng/ml, about 50 ng/ml, about 60 ng/ml, about 70 ng/ml, about 80 ng/ml, about 90 ng/ml, or about 100 ng/ml.

In an embodiment, the FGF component is a FGF other than bFGF and is at a concentration equivalent to from about 0.25-100 ng/ml or any 0.1 ng/ml increment there between of bFGF.

In an embodiment, the cardiovascular mesoderm cells are incubated with the FGF component for about 2 to about 7 days, optionally about 2 days, about 3 days, about 4 days or about 5 days.

As shown herein, cardiovascular progenitors can express TBX18 and can give rise to SANLCM using methods described herein. Also cardiovascular progenitors can express NKX2-5 and give rise to VLCM.

In an embodiment, the cardiovascular mesoderm cells are produced from embryoid bodies, the method comprising:

incubating embryoid bodies in a mesoderm induction medium comprising a BMP component, optionally BMP4, and an activin component, optionally Activin A, and optionally a FGF component, optionally bFGF, for a period of time to generate cardiovascular mesoderm cells. Methods for producing cardiomyocyte populations including embryoid bodies and cardiovascular mesoderm cells are disclosed in PCT application no. PCT/CA2014/000687 (entitled METHODS AND COMPOSITIONS FOR GENERATING EPICARDIUM CELLS) filed on Sep. 12, 2014 which is herein incorporated by reference in its entirety.

Embryoid bodies can be obtained by incubating hPSCs in an embryoid body medium comprising a BMP component, optionally BMP4, optionally further comprising a Rho-associated protein kinase (ROCK) inhibitor, for a period of time to generate embryoid bodies.

In another embodiment, embryoid bodies used to obtain cardiovascular mesoderm cells can be obtained by incubating hPSCs in an embryoid body medium comprising a BMP component, optionally BMP4, optionally further comprising a Rho-associated protein kinase (ROCK) inhibitor, for a period of time to generate embryoid bodies.

In an embodiment, cardiovascular mesoderm cells can be obtained by incubating embryoid bodies in a mesoderm induction medium comprising a BMP component, optionally BMP4, and an activin component, optionally Activin A and optionally a FGF component, optionally bFGF, for a period of time to generate cardiovascular mesoderm cells.

Accordingly, another aspect includes a method of producing a population of cardiomyocytes enriched for sinoatrial node-like pacemaker cardiomyocytes (SANLCM) from human pluripotent stem cells (hPSCs), the steps comprising:
  a. incubating the hPSCs in an embryoid body medium comprising a BMP component, optionally BMP4, optionally further comprising a Rho-associated protein kinase (ROCK) inhibitor, for a period of time to generate embryoid bodies;
  b. incubating the embryoid bodies in a mesoderm induction medium comprising a BMP component, optionally BMP4, and an activin component, optionally Activin A and optionally a FGF component, optionally bFGF, for a period of time to generate cardiovascular mesoderm cells;
  c. incubating the cardiovascular mesoderm cells in a cardiac induction medium comprising a BMP component, optionally BMP4, above a selected amount, and retinoic acid (RA), and optionally one or more of a FGF inhibitor, a WNT inhibitor, optionally IWP2, VEGF and an activin/nodal inhibitor, optionally SB-431542; for a period of time to generate cardiovascular progenitor cells that express TBX18, wherein the cardiovascular mesoderm cells are preferably incubated with the FGF inhibitor and which FGF inhibitor is provided for all or part of the cardiac induction phase;
  d. incubating the cardiovascular progenitor cells in a basic medium comprising VEGF for a period of time to generate a population of cardiomyocytes enriched for SANLCMs; and
  e. optionally isolating the population of cardiomyocytes enriched for SANLCMs using a cardiomyocyte-specific surface marker, optionally wherein the marker is signal-regulatory protein alpha (SIRPA), optionally wherein the isolated population is SIRPA$^{pos}$ CD90$^{neg}$.

As demonstrated herein, any human pluripotent stem cell line can be used, including for example embryonic stem cell lines and induced pluripotent stem cells (iPSCs) derived for example from patient blood or skin samples. Methods for producing iPSCs are known in the art iPSCs can be derived from multiple different cell types, including terminally differentiated cells. iPSCs have an ES cell-like morphology, and express one or more key pluripotency markers known by one of ordinary skill in the art, including but not limited to Alkaline Phosphatase, SSEA3, SSEA4, Sox2, Oct3/4, Nanog, TRA160, TRA181, TDGF 1, Dnmt3b, FoxD3, GDF3, Cyp26a1, TERT, and zfp42. Examples of methods of generating and characterizing iPSCs may be found in, for example, U.S. Patent Publication Nos. US20090047263, US20090068742, US20090191159, US20090227032, US20090246875, and US20090304646, the disclosures of which are incorporated herein by reference. Generally, to generate iPSCs, somatic cells are provided with reprogramming factors (e.g. Oct4, SOX2. KLF4, MYC, Nanog, Lin28, etc.) known in the art to reprogram the somatic cells to become pluripotent stem cells.

As shown herein, hPSC lines can be used to produce cultures enriched for SANLCMs which can be further enriched/purified using cell sorting. For example, in embodiments where FGF inhibitors are used to increase the proportion of SANLCMs (which reduces the NKX2-5+ cTNT+ cardiomyocyte population) selection of cardiomyocytes from these cultures by Flow assisted cells sorting (FACS) for SIRPA$^+$ and CD90$^-$ cells achieves cultures highly enriched in SANLCMs (e.g. 70-90%).

In an embodiment, the hPSCs are induced pluripotent stem cells (iPSCs). In an embodiment, the hPSCs are human embryonic stem cells (hESCs).

In other embodiments, mammalian PSCs are used in the methods described herein, including for example but not limited to rodent such as mouse and rat PSCs, non-human primate PSCs and pig PSC.

In an embodiment, the hESCs are H7 cells, HES2 cells or HES3 cells. In an embodiment, the iPSCs are MSC-iPS1 cells. In a further embodiment, the iPSCs are prepared from cells obtained from a subject.

iPSCs can be produced according to known methods such as the methods disclosed in U.S. Pat. Nos. 8,278,104 and 8,058,065 which are herein incorporated by reference In some embodiments, hPSCs (or mammalian PSCs) comprising a reporter construct are used to monitor development of cardiac populations. In an embodiment, the hPSCs are hPSCs comprising a NKX2-5 reporter construct.

In an embodiment, the BMP component is BMP4. In another embodiment, the BMP component is BMP2.

In another embodiment, isolating or purifying the population of cardiomyocytes enriched for SANLCMs comprises:

a. isolating SIRPA marker positive cardiomyocytes; and/or
b. selecting cardiomyocytes negative for NKX2-5 expression and/or negative for CD90 expression.

In another embodiment, isolating the population of cardiomyocytes substantially devoid of SANLCMs comprises:
a. isolating SIRPA marker positive cardiomyocytes; and/or
b. selecting cardiomyocytes positive for NKX2-5 expression and/or negative for CD90 expression.

As demonstrated herein, to isolate a population enriched for cardiomyocytes, a cardiomyocyte cell-surface marker can be used. For example, SIRPA is a cardiomyocyte specific cell-surface marker that can be used for isolating cardiomyocytes derived from human pluripotent stem cells.[10] For instance, cells such as stem cell differentiation cultures can be sorted with an antibody against SIRPA. In Dubois et al.[10], it was shown that cell sorting with an antibody against SIRPA yielded population of up to 98% cardiac troponin T (cTnT)-positive cells.

NKX2-5 or homeobox protein NKX2-5 is a transcription factor involved in the regulation of cardiomyocyte formation. It is expressed in some cardiomyocyte subtypes such as ventricular cardiomyocytes but not in others, such as SANLCMs.

It is demonstrated herein that selecting NKX2-5 negative cells enriches for SANLCMs and selecting NKX2-5 positive cells from cultures treated with cardiac induction medium comprising FGF as described herein enriches for ventricular-like cardiomyocytes. Selecting for NKX2-5 cells can be used for example in methods using a NKX2-5 reporter assay. Measuring NKX2-5 expression levels can also be used to confirm that a population obtained is the desired population and/or to confirm the amount of undesired cells. For example, an aliquot of a cardiomyoctye population treated according to methods described herein for enriching for SANLCMs can tested to confirm that level of NKX2-5 expression is low (e.g. as in an unpurified population) or virtually absent (e.g. as in a population that is purified for SIRPApos CD90neg cells). Similarly, an aliquot of a cardiomyoctye population treated according to methods described herein for producing a population substantially devoid of SANLCMs (e.g. using VEGF and IWP2 in the cardiac induction phase) can be tested to confirm that the level of NKX2-5 expression is high.

As demonstrated NKX2-5 negative selected cardiomyocytes are cardiomyocytes enriched for SANLCMs.

In another embodiment, NKX2-5 positive selected cardiomyocytes are cardiomyocytes enriched for ventricular-like cardiomyocytes (VLCMs).

For example, a NKX2-5 reporter construct can be used to identify cardiomyocytes such as stem cell derived cardiomyocytes. As shown in Elliott et al.[16], sequences encoding enhanced GFP were introduced into the NKX2-5 locus by homologous recombination and NKX2-5:GFP positive hESCs differentiated into cardiac progenitor cells.

Fluorescence detection techniques such as immunofluorescence analysis can be used to select or determine NKX2-5 eGFP expressing cells. For example, the presence of fluorescence in reporter cells is indicative that the cell expresses NKX2-5. For example, the absence of fluorescence is indicative that the cell does not express NKX2-5 or does not express high levels of NKX2-5. Other NKX2-5 reporter constructs can also be used.

Cells can be isolated for example using flow cytometry (e.g. FACS) based on marker expression (e.g. cell surface markers) and/or when using fluorescent based reporters.

Other methods can be used with other reporters, for example cells comprising an antibiotic resistant reporter gene can be isolated based on their antibiotic resistance to for example Geneticin®, Puromycin or Hygromycin B.

Other reporter constructs can be used to produce a population of cardiomyocytes enriched for SANLCMs. For example, SAN specific markers can be used. In an embodiment, the reporter construct is a SHOX-2 reporter construct. In another embodiment, the reporter construct is a TBX18 reporter construct.

While it is not necessary to use a NKX2-5 reporter construct to produce a population of cardiomyocytes enriched for SANLCMs, using an hPSC cell line comprising a NKX2-5 reporter or introducing a NKX2-5 reporter construct in a stem cell such as a hPSC line can be used to monitor and/or optimize the SANLCM differentiation protocol, e.g. the presence of NKX2-5 expression can be measured and the protocol can be adjusted accordingly until a absence and/or minimum desirable presence of NKX2-5 expression is detected by for example immunofluorescence analysis.

Alternatively, the method of producing a population of cardiomyocytes enriched for SANLCMs described above can comprise the use of an antibody specific for NKX2-5. For example, an antibody to NKX2-5 such as rabbit anti-human NKX2-5 (1:800, Cell Signaling Technology) can be used.

For example, an aliquot of a cell culture can be assessed to measure the level of NKX2-5 and/or one or more markers described herein to assess for example that a desired level or number of cells are expressing a marker associated with a stage described herein. The cell culture can be tested at one or more stages and/or upon completion to measure for example the number of SANLCMs produced. The level of one or more markers (cell surface or intracellular) can be measured using immuno-based methods for example, flow cytometry, including FACS, or mRNA expression based methods such as quantitative RT-PCR, In an embodiment, the population of cardiomyocytes enriched for SANLCMs comprises at least or about 30% of SANLCMs, at least or about 50% of SANLCMs, at least or about 70% of SANLCMs, or at least or about 90% of SANLCMs.

In an embodiment, the population of cardiomyocytes enriched for VLCMs comprises at least or about 15% of VLCMs, at least or about 20% of VLCMs, at least or about 30% of VLCMs, at least or about 50% of VLCMs, at least or about 70% of VLCMs, or at least or about 90% of VLCMs.

FIG. 1A illustrates a scheme of the developmentally staged protocol for the hESC differentiation into cardiomyocytes. In an embodiment, the hPSCs are incubated in the embryoid body medium at day 0 of the differentiation process. In an embodiment, the embryoid bodies are incubated in the mesoderm induction medium from about day 1 to about day 3 of the differentiation process. In an embodiment, the cardiovascular mesoderm cells are incubated in the cardiac induction medium from about day 3 to about day 5 of the differentiation process. In an embodiment, the cardiovascular progenitor cells are incubated in a basic medium from about day 5 to about day 20 of the differentiation process.

In an embodiment, the hPSCs are incubated in the embryoid body medium to generate embryoid bodies from about 6 hours to about 2 days, optionally 18 hours.

In an embodiment, the embryoid bodies are incubated in the mesoderm induction medium to generate cardiovascular mesoderm cells for about 1 to about 4 days, optionally 2 days.

In an embodiment, the cardiovascular mesoderm cells are incubated in the cardiac induction medium to generate cardiovascular progenitor cells for about 1 to about 4 days, optionally 2 days.

In an embodiment, the cardiovascular progenitor cells are incubated in the basic medium to generate cardiomyocytes for about 4 or more days, optionally about 4, about 5, about 9, about 15 or about 20 days. In an embodiment, the cardiovascular progenitor cells are incubated in the basic medium to generate cardiomyocytes from about 4 days to about 20 days or any number of days between 4 days and 20 days. In an embodiment, the cardiovascular progenitor cells are incubated in the basic medium to generate cardiomyocytes for over 20 days.

In an embodiment, the mesoderm induction medium comprises BMP4 at a concentration ranging between about 0.5 ng/mL to about 5 ng/mL, between about 0.5 ng/mL to about 3 ng/mL, between about 0.5 ng/mL to about 8 ng/mL, between about 2 ng/mL to about 10 ng/mL, between about 0.5 ng/mL to about 10 ng/mL, or between 0.5 ng/mL to about 20 ng/mL. The concentration can be or range from any 0.1 ng/mL increment between about 0.5 ng/mL up to about 20 ng/mL.

In an embodiment, the mesoderm induction medium comprises BMP4 at a concentration of about 1 ng/mL, about 2 ng/mL, about 3 ng/mL, about 4 ng/mL, about 5 ng/mL, about 8 ng/mL, or about 10 ng/mL, or up to about 20 ng/mL, optionally about 3 ng/mL.

In an embodiment, the mesoderm induction medium comprises Activin A at a concentration ranging between about 0.5 ng/mL to about 3 ng/mL, between about 0.5 ng/mL to about 4 ng/mL, between about 0.5 ng/mL to about 5 ng/mL, between about 1 ng/mL to about 10 ng/mL, between about 1 ng/mL to about 20 ng/mL, between 0.1 ng/mL to about 10 ng/mL, or between 0.1 ng/mL to about 20 ng/mL. The concentration can be or range from any 0.1 ng/mL increment between about 0.1 ng/mL up to about 20 ng/mL.

In another embodiment, the mesoderm induction medium comprises Activin A at a concentration of about 1 ng/mL, about 2 ng/mL, about 3 ng/mL, about 5 ng/mL, about 8 ng/mL, about 10 ng/mL, or about 20 ng/mL, optionally about 2 ng/mL.

In an embodiment, the mesoderm induction medium comprises BMP4 at a concentration of about 3 ng/mL and Activin A at a concentration of about 2 ng/mL.

BMP4 signaling plays an important role in the specification of the pacemaker population at the mesoderm stage (around day 3) and as such an adequate dosing and time of treatment with BMP4 is important in the generation of cardiomyocytes enriched for SANLCMs. It was previously shown that blocking BMP signaling and exposure to high levels of BMP4 resulted in a significant reduction of cardiomyocytes. As shown in FIG. 2B-D and FIG. 7B, lower levels of BMP4 lead to an increase in the proportion of SANLCMs.

In an embodiment, the cardiovascular mesoderm cells are treated with cardiac induction medium comprising BMP4 for about 1 day to about 4 days, optionally 2 days, at concentrations of about 0.5 ng/mL, about 1.0 ng/mL, about 1.5 ng/mL, about 2.0 ng/mL, about 2.5 ng/mL, about 3.0 ng/mL, about 5.0 ng/mL, about 10.0 ng/mL, about 20.0 ng/mL, about 30.0 ng/mL, about 40.0 ng/mL, about 50.0 ng/mL, about 60.0 ng/mL, about 70.0 ng/mL, or about 80.0 ng/mL, optionally 2.5 ng/mL.

Figure 3:
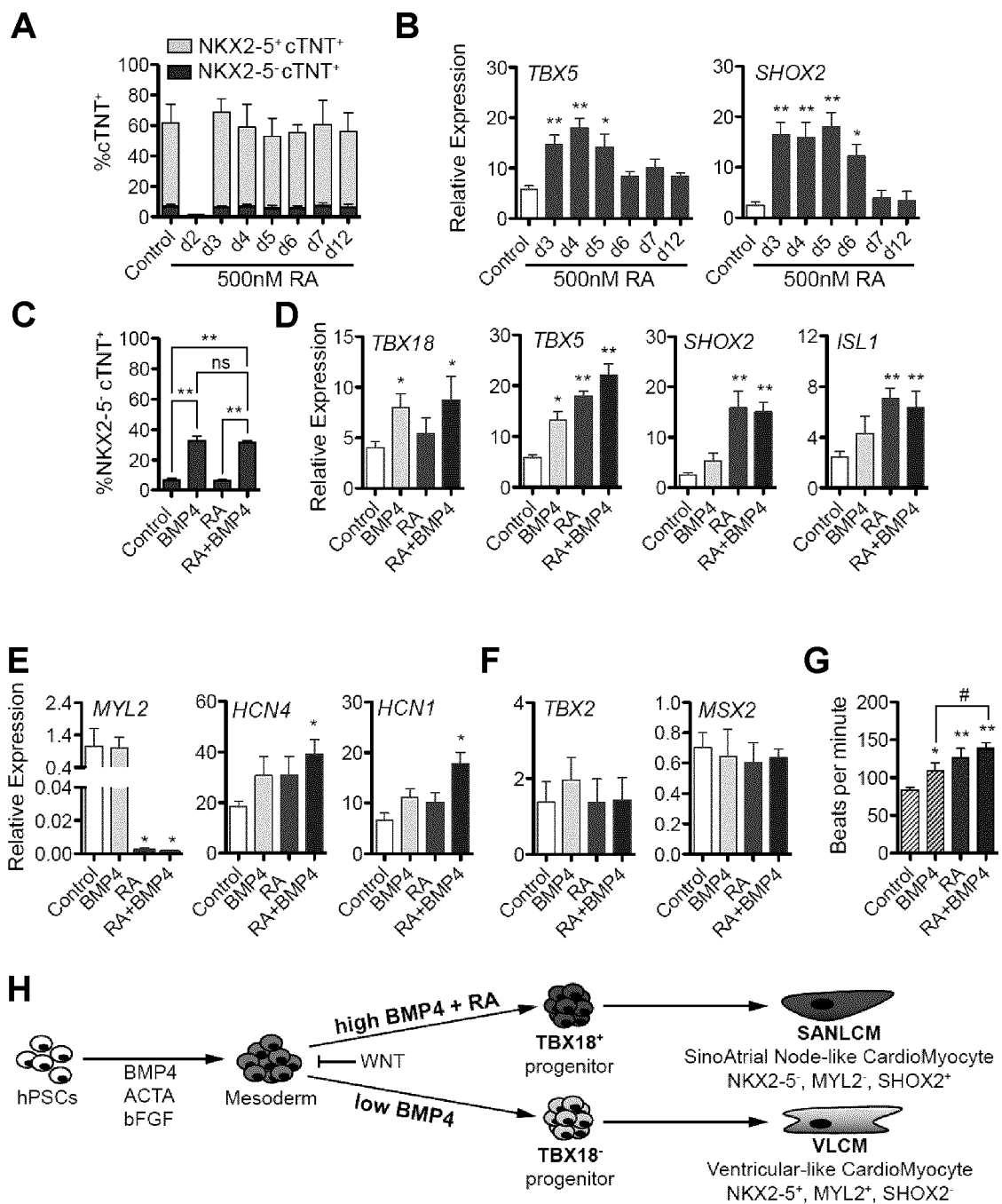
FIG. 3. Retinoic acid signaling enhances SAN pacemaker phenotype. A, Summary of FACS results analyzing the effect of retinoic acid (RA) treatment at different time points during differentiation on the size of the NKX2-5$^-$cTNT$^+$ SANLCM population (n=4). B, Q-PCR analysis of TBX5 and SHOX2 at day 20 of differentiation in NKX2-5$^-$SIRPA$^+$ sorted SANLCM from cultures that were treated with RA at indicated time points. Expression relative to the housekeeping gene TBP. T-test: *P<0.05, P<0.01 vs untreated control (n=4). C, Summary of FACS results for the effect of BMP4 (day 3-5), RA (day 3) and combined RA/BMP4 treatment on the size of the SANLCM population. T-test: P<0.01 D-F, Q-PCR analysis of the effect of BMP4, RA and combined RA/BMP4 treatment on the expression of: SAN pacemaker marker (D), ventricular marker and cardiac ion channels (E) and AVN pacemaker marker (F) in NKX2-5$^-$SIRPA$^+$ sorted SANLCM from day 20 cultures. Expression relative to the housekeeping gene TBP. T-test: *P<0.05, **P<0.01 vs untreated control (n=5). G, Effect of BMP4, RA and combined RA/BMP4 treatment on the beating rates of SANLCM at day 20 of differentiation. T-test: *P<0.05, **P<0.01 vs untreated control, #P<0.05, vs indicated sample (n=10). H, Summary Scheme of suggested model of SANLCM lineage specification from hPSCs by BMP4 and RA signaling. Error bars show s.e.m. d, day; RA, retinoic acid.

As shown in FIG. 3, RA signaling also impacts the development of SANLCMs. While adding RA at day 2 of the differentiation process blocked the generation of cardiomyocytes, adding RA at later times had no effect on total cardiomyocytes or SANLCM frequency. It is shown herein that addition of RA between days 3 and 5 significantly upregulates the posterior cardiomyocyte marker TBX5 and the SAN marker SHOX2. It is demonstrated that RA signaling enhances the pacemaker phenotype in SAN progenitors (FIG. 3H).

In an embodiment, the cardiovascular mesoderm cells are treated with cardiac induction medium comprising RA for about 1 day to about 4 days, optionally 1 day, at concentrations of about 50 ng/mL, about 100 ng/mL, about 150 ng/mL, about 200 ng/mL, about 300 ng/mL, about 400 ng/mL, about 500 ng/mL, or about 1000 ng/mL, optionally 150 ng/mL or any concentration or range from any 0.1 ng/mL increment between about 50 ng/mL up to about 1000 ng/mL (alternatively about 100 nM to about 3 mM or any 1 nM increment between 100 nM and 3 mM.

In an embodiment, the RA is all-trans RA (Sigma R2625) or 9-cis RA (Sigma R4643) at a concentration ranging between about 20 ng/ml to about 1000 ng/ml, optionally at a concentration of about 150 ng/mL.

In another embodiment, the RA is a RA analog. In an embodiment, the RA analog is AM580, a selective RARα agonist (Tocris 0760) at a concentration ranging from about 1 ng/ml to about 500 ng/ml, optionally at a concentration of about 18 ng/mL. In an embodiment, the RA analog is AC55649, a selective RARβ agonist (Tocris 2436) at a concentration ranging from about 10 ng/ml to about 1000 ng/ml, optionally at a concentration of about 80 ng/mL. In an embodiment, the RA analog is CD437, a selective RARγ agonist (Tocris 1549) at a concentration ranging from about 50 ng/ml to about 5000 ng/ml, optionally at a concentration of about 600 ng/mL.

Figure 2:
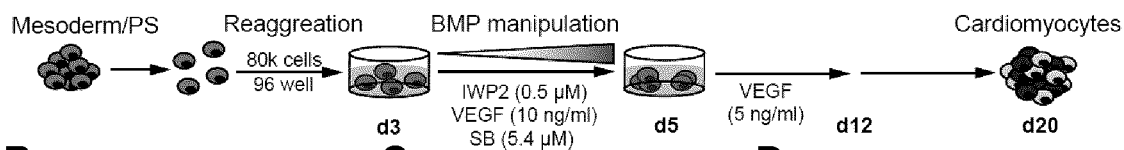
FIG. 2. BMP4 signaling specifies the SANLCM pacemaker population. A, Scheme of modified differentiation protocol with dissociation of EBs at the mesoderm stage (day 3) to efficiently deliver signaling molecules. B-D, Summary of day 20 FACS results for NKX2-5 and cTNT after BMP4 titration from day 3-5 in cultures that were induced for mesoderm formation with: 10 ng/ml BMP4, 6 ng/ml ACTA (B); 5 ng/ml BMP4, 4 ng/ml ACTA (C); 3 ng/ml BMP4, 2 ng/ml ACTA (D). T-test: *P<0.05, **P<0.01 vs NKX2-5$^-$ CTNT$^+$ cells at endogenous (E) BMP4 levels (n=4). E, Representative FACS plots at day 20 of differentiation, showing the increase of the NKX2-5$^-$cTNT$^+$/NKX2-5$^-$SIRPA$^+$ SANLCM population in cultures treated with 2.5 ng/ml of BMP4 from day 3-5 of differentiation. F, Summary of FACS results analyzing the time window of BMP4 treatment that is efficient to increase the SANLCM population. T-test: *P<0.05, **P<0.01 vs untreated control (n=3). G, Q-PCR analysis of TBX18 expression in untreated control vs BMP4 (day 3-5, 2.5 ng/ml) treated cultures from day 4 to day 12 of differentiation (n=3). H, Quantification of TBX18$^+$ cells from immunostaining (n=3). I, Immunostaining for TBX18 in control and BMP4 treated cultures at day 6 of differentiation. DAPI was used to counterstain cell nuclei. Scale bars represent 100 µm. Error bars show s.e.m. T-test: *P<0.05, **P<0.01. d, day; Dorso, dorsomorphin; E, endogenous/untreated.
Figure 2:
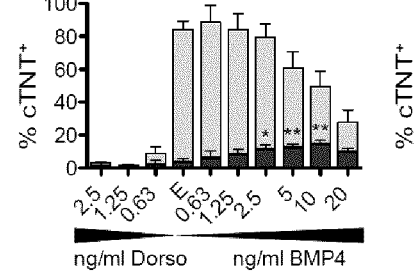
Figure 2:
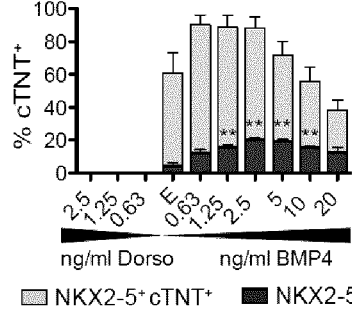
Figure 2:
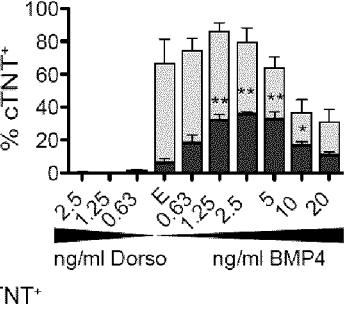
Figure 2:
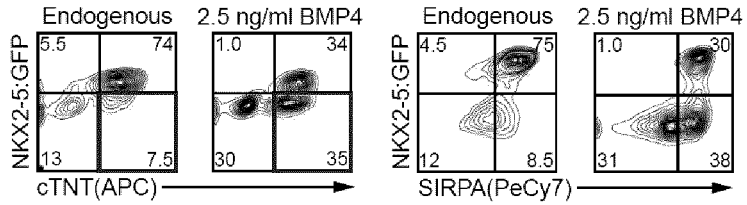
Figure 2:
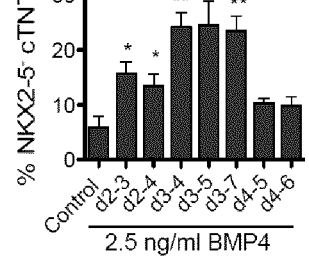
Figure 2:
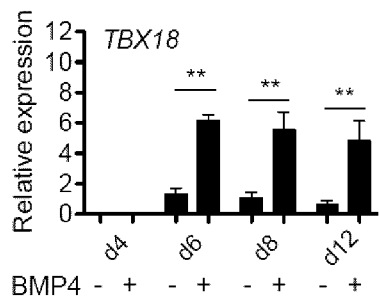
Figure 2:
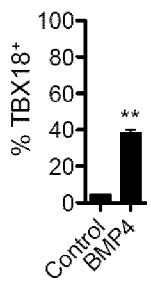
Figure 2:
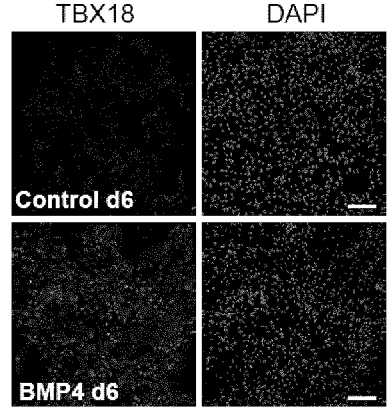

It is shown herein that combined treatment of cardiovascular mesoderm cells with BMP4 and RA between days 3 and 5 increases the SANLCM differentiation process. As shown in FIG. 3, combined RA/BMP4 signaling significantly increased the expression of the pacemaker ion channel genes HCN4 and HCN1 (FIG. 3F) but not the AVN specific genes TBX2 and MSX2. Also, combined RA/BMP4 signaling significantly increased the beating rate of the cells (FIG. 2G). Further, treatment of RA alone and in combination of BMP4 increased the expression of TBX5, SHOX2 and ISL1 (FIG. 3E) but decreased the expression of MYL2 (a ventricular marker).

In another embodiment, the cardiovascular mesoderm cells are treated with BMP4 and RA. In yet another embodiment, the cardiovascular mesoderm cells are treated with BMP4 at a concentration of about 2.5 ng/mL and RA at a concentration of about 150 ng/mL.

In another embodiment, the cardiovascular mesoderm cells are treated with BMP2 and RA. In some embodiments, the cardiovascular mesoderm cells are treated with RA (e.g. in the absence of BMP component).

As demonstrated in FIG. 12, treating cardiovascular mesoderm cells with FGF inhibitor increases the proportion of SANLCMs. Without wishing to be bound by theory, inhibition FGF signaling removes the NKX2-5$^{pos}$ cTNT$^{pos}$ cardiomyocyte population.

Further, as shown in FIG. 12A treating cardiovascular mesoderm cells with FGF decreases the proportion of SAN-LCMs and generates NKX2-5pos cardiomyocyte cultures that are substantially devoid of SANLCMs. Without wishing to be bound by theory, FGF signaling removes the NIKX2-5$^{neg}$cTNT$^{pos}$ cardiomyocyte population and any pacemaker cells.

Accordingly in another embodiment, the cardiovascular mesoderm cells are treated with BMP2, RA and FGF inhibitor, optionally PD173074. In other embodiments the cardiovascular mesoderm cells are treated with BMP2, RA and FGF, optionally bFGF.

In an embodiment, the cardiovascular mesoderm cells are incubated at least until they express a desired level of MESP1, PDGFRalpha and/or KDR and/or a desired proportion of cells expressing MESP1, PDGFRalpha and/or KDR.

MESP1, KDR and/or PDGFRalpha can be used to monitor the development of cardiovascular mesoderm cells. For example, using immune-based methods, the expression of KDR can be monitored for example by FACs using an antibody specific for KDR. The expression of PDGFRalpha can be monitored by FACS using an antibody specific for PDGFRalpha. These markers can by monitored using flow cytometry. For example, the expression of MESP1, KDR and PDGFRalpha can be monitored and/or cells expressing these markers can be isolated using cell sorting, for example FACS or other immunostaining methods.

In another embodiment, the cardiovascular progenitor cells and/or cardiomyocytes are incubated until they express a desired level of cardiac troponin T (cTnT).

cTNT can be used to monitor the development of cardiomyocytes. The expression of cTNT can be used to monitor using an antibody specific for cTNT, for example anti-cardiac isoform of cTNT (clone 13-11; 1:2000, Thermo Fischer). The expression of cTNT can be monitored using flow cytometry, for example FACS. The expression of cTNT can also be monitored by immunostaining.

CD90 is a cell surface mesenchymal marker that can be used to isolate non-myocyte populations in differentiation cultures. In an embodiment, CD90 can be used to deplete non-myocytes and/or to isolate cardiomyocytes.

In another embodiment, cardiomyocyte subtypes SANLCMs and VLCMs can be sorted, for example by FACS, according to NKX2-5, SIRPA and CD90 expression. For example, as shown in FIGS. 1D and 5C, cardiomyocyte populations are sorted for NKX2-5$^+$SIRPA$^+$CD90$^-$ and NKX2-5$^-$SIRPA$^+$CD90$^-$ populations at day 20 of differentiation.

TBX18, SHOX2 and TBX3 are SAN specific markers. In an embodiment, cardiomyocytes enriched for SANLCMs express an increased level of TBX18, SHOX2 and/or TBX3 compared to cardiovascular mesoderm cells not treated with the BMP component and RA.

MYL2 and IRX4 are ventricular cardiomyocyte specific markers. In an embodiment, cardiomyocytes enriched for SANLCMs express lower levels of MYL2 and IRX4 compared to cardiovascular mesoderm cells not treated with the BMP component and RA.

It is demonstrated herein that SANLCMs have significantly faster spontaneous action potential rates compared to VLCMs (FIG. 4A-B).

In an embodiment, the SANLCMs have a minimum or average spontaneous beating rate of at least 50 beats per minute (BPM), at least 60 BPM, at least 80 BPM, at least 90 BPM, at least 100 BPM, at least 110 BPM, at least 120 BPM, at least 140 BPM at least 160 BPM at least 180 BPM, up to about 200 BPM.

Beating rates can be measured to assess the functionality of SANLCMs as pacemakers. As described in Example 1, the functionality of SANLCMs can be determined by isolating ventricular-like cardiomyocytes (VLCMs), optionally by FACS, and forming electrically integrated monolayers on for example a multi-electrode array. Aggregates of SANLCMs are placed on the VLCM monolayers and cultured to allow electrical integration. It is shown that the SANLCM aggregate can stably initiate and propagate electric activity through the adjacent monolayer and as a result increase the beating frequency from 63.1±2.5 to 112.5±18.5 bpm (Table 2).

Another aspect includes a method of isolating SANLCMs or VLCMs from a population of cardiomyocytes comprising a) producing a population of cardiomyocytes from hPSCs comprising a NKX2-5 reporter construct, optionally according to a method described herein and b) selecting NKX2-5 negative or positive cardiomyocytes.

In an embodiment, the NKX2-5 reporter construct is a fluorescent NKX2-5 reporter construct.

In an embodiment, the fluorescent reporter comprises a GFP (optionally enhanced GFP) reporter gene. Other fluorescent proteins as well as non-fluorescent markers can be used.

In an embodiment, one or more or all of the steps of a method described herein are performed in vitro.

A further aspect includes an isolated population of cardiomyocytes enriched for SANLCMs comprising at least or about 30% of SANLCMs, at least or about 50% of SANLCMs, at least or about 60% of SANLCMs, at least or about 70% of SANLCMs, at least or about 80% of SANLCMs or at least or about 90% of SANLCMs, obtained according to a method described herein.

A further aspect includes an isolated population of cardiomyocytes enriched for VLCMs comprising at least or about 15% of VLCMs, at least or about 20% of VLCMs, at least or about 30% of VLCMs, at least or about 50% of VLCMs, at least or about 60% of VLCMs, at least or about 70% of VLCMs, at least or about 80% of VLCMs or at least or about 90% of VLCMs, obtained according to a method described herein.

Another aspect includes a SANLCM or VLCM comprising a NKX2-5 reporter construct or a population of SANLCMs comprising a NKX2-5 reporter construct obtained according to the method herein described.

A further aspect includes various uses of the isolated population of cardiomyocytes, for example cardiomyocytes substantially devoid (VLCM) or enriched for SANLCMs. Uses include transplant, for example for in vivo pacemaking (SANLCM) or for remuscularization after myocardial infarction (VLCM) in a subject, disease modelling and testing candidate drugs. Other uses include studying the safety pharmacology testing of drugs (not developed to treat heart conditions) for potential side effects on SANLCM and VLCM, the development of SAN pacemaker or VLCM cells using the human stem cell system, and studying the physiology of human SAN pacemaker and VLCM as healthy human samples are not readily available.

Accordingly a further aspect is a method of identifying a candidate drug comprising:
 a. generating a SANLCM according to a method described herein;
 b. contacting the SANLCM with a candidate test drug;
 c. measuring the beat rate, action potential characteristics and/or ion currents of the SANLCM;
 d. comparing the beat rate, the action potential characteristics and/or ion currents of the SANLCM to a control SANLCM not treated with the candidate test drug; and e. selecting the candidate test drug which modulates the beat rate and/or action potential compared to the control cell as the candidate drug.

In an embodiment, the SANLCM is comprised in a population of cardiomyocytes enriched for SANLCMs.

Figure 4:
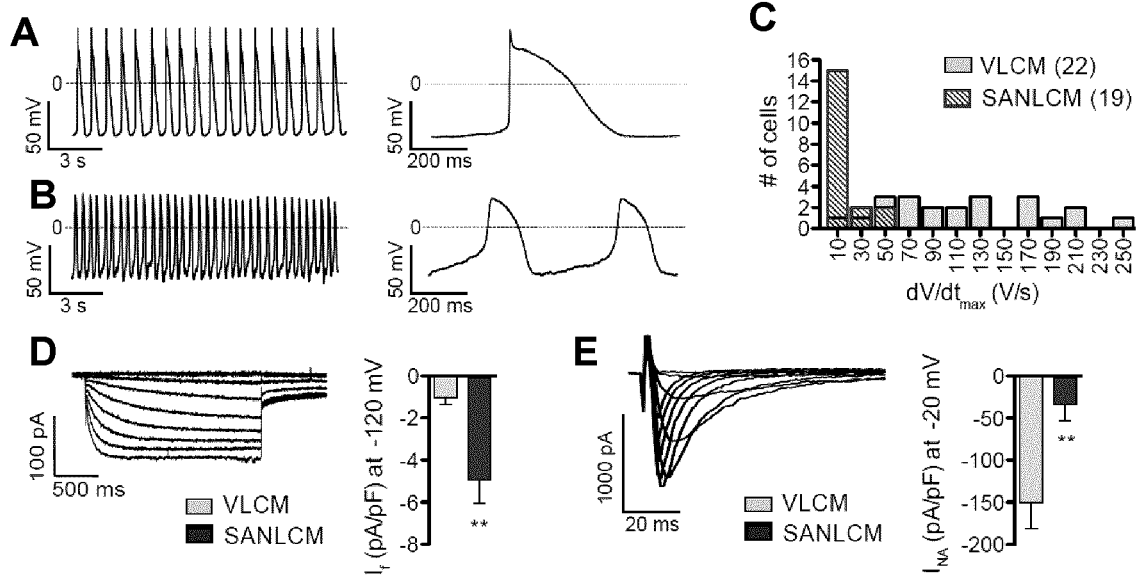
FIG. 4. SANLCM have functional pacemaker character. A,B, Original traces of spontaneous action potentials recorded for NKX2-5$^+$SIRPA$^+$ sorted VLCM (A) and NKX2-5$^-$ SIRPA$^+$ sorted SANLCM (B). C, Histogram plot showing the distribution of the maximum upstroke velocities (dV/dt$_{max}$) recorded in SANLCM and VLCM. D, Original traces of pacemaker funny current (I$_f$) at different membrane potentials, recorded in SANLCM and average of maximum I$_f$ current density at −120 mV in VLCM and SANLCM (n=12). E, Original traces of sodium current (I$_{Na}$) at different membrane potentials, recorded in VLCM and average of maximum I$_{Na}$ current density at −20 mV in VLCM and SANLCM (n=11). T-test: **P<0.01 vs VLCM. F, Scheme of experimental setup used for in-vitro pacing experiments of VLCM monolayers cultured on multi-electrode arrays. G-I, VLCM monolayer before addition of SANLCM aggregate. Low magnification bright field picture of VLCM monolayer (G). Representative greyscale-map of electrical signal propagation in the depicted monolayer. The greyscale-map represents a snapshot of the electrical propagation in the monolayer and shows that the electrical signal is initiated at the bottom left corner (white) and is propagated to the upper right corner (black) (H). Beating rate of the monolayer in beats per minute (bpm) presented as original field potentials recorded at electrode 65 (I). J-L, VLCM monolayer after addition of Tetramethylrhodamine methyl ester (TMRM) labeled SANLCM aggregate. Low magnification bright field and TMRM, GFP channel pictures. The SANLCM aggregate is located on top of electrode 65. Insets: 2.5-fold magnification (J). Representative greyscale-map of electrical propagation in the monolayer after placing the SANLCM aggregate. Original field potentials recorded at electrodes 65, 46, and 28 highlight that the electrical signal is initiated by the SANLCM aggregate (electrode 65) (K). Beating rate of the culture in beats per minute (bpm) depicted below as original field potentials recorded at electrode 65 and electrode 28 (L). Scale bars represent 250 µm. Error bars show s.e.m.
Figure 4:
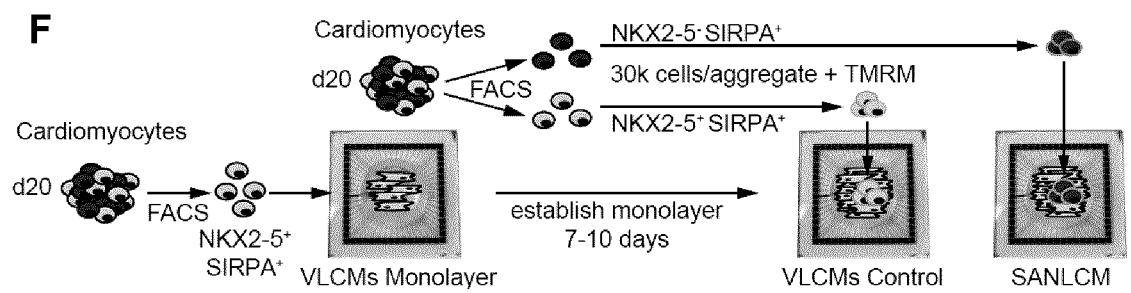
Figure 4:
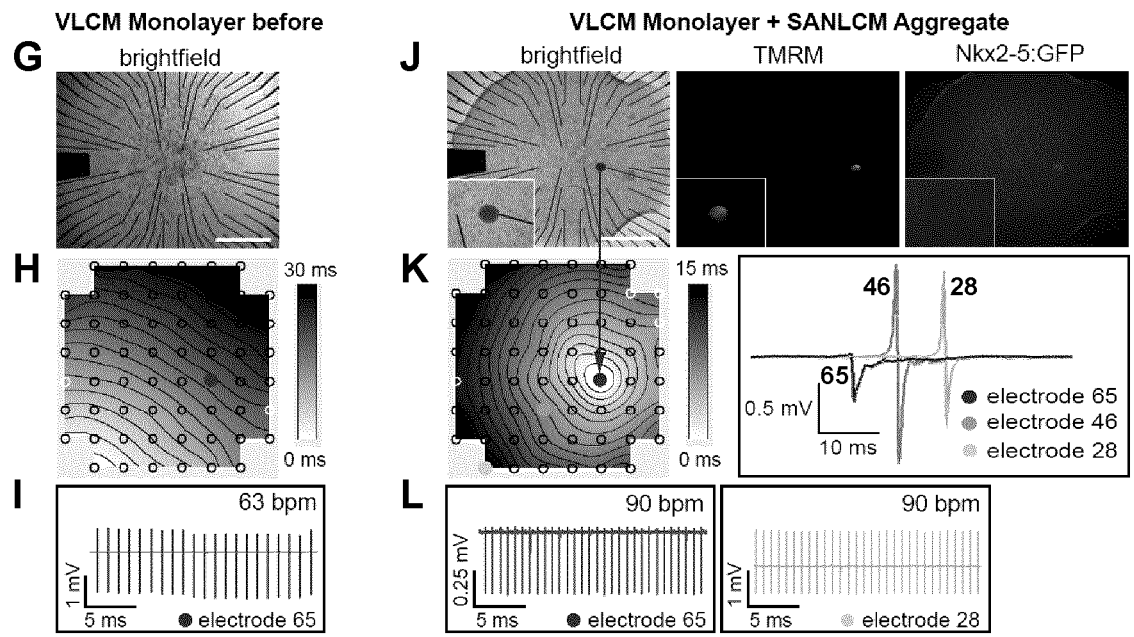

Various methods known in the art can be used to measure the action potential in a cell. In an embodiment, the action potential in a cell is measured using low throughput patch clamp (as shown in FIG. 4 A-E).

Figure 10:
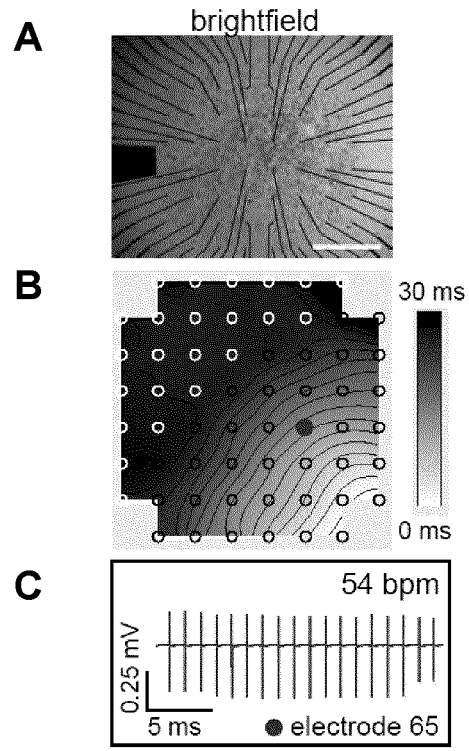
FIG. 10. A-C, VLCM Monolayer before addition of VLCM control aggregate. Low magnification bright field picture of VLCM Monolayer (A). Representative greyscale-map of electrical signal propagation in the depicted monolayer. The greyscale-map represents a snapshot of the electrical propagation in the monolayer and shows that the electrical signal is initiated at the bottom right corner (white) and is propagated to the upper left corner (black) (B). Beating rate of the monolayer in beats per minute (bpm) presented as original field potentials recorded at electrode 65 (C). D-F, VLCM Monolayer after addition of Tetramethyl-rhodamine methyl ester (TMRM) labeled VLCM control Aggregate. Low magnification bright field and TMRM, GFP channel pictures. VLCM control Aggregate is located on top of electrode 65. Insets: 2.5-fold magnification. Note, the VLCM monolayer and the VLCM control aggregate are NKX2-5:GFP⁺ (D). Representative greyscale-map of electrical propagation in the monolayer after placing the VLCM control aggregate. Original field potentials recorded at electrodes 65, 46, and 28 highlight that the electrical signal is not initiated by the control VLCM aggregate (electrode 65) (E). Beating rate of the culture in beats per minute (bpm) depicted below as original field potentials recorded at electrode 65 and electrode 28 (F). Scale bars represent 250 µm.
Figure 10:
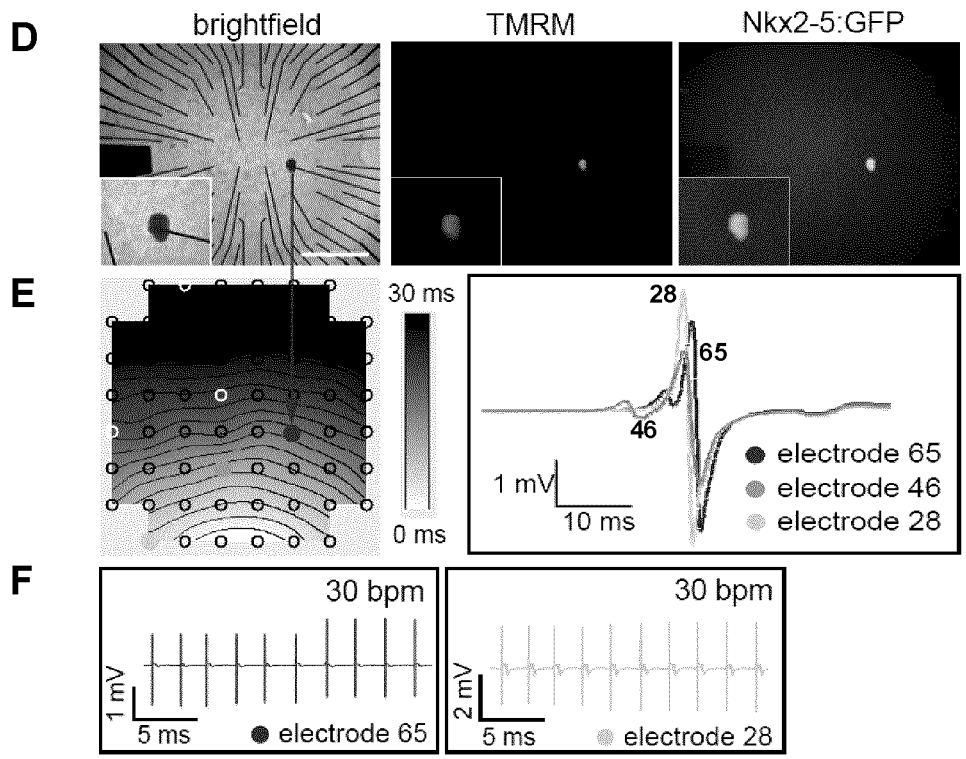

In an embodiment the electric signals in a cell are measured using multi-electrode arrays (MEA) (see FIG. 4F and FIG. 10). The MEA system is a medium throughput system which records field potentials that can be indicative of drug effects on ion-channels/currents.

An in-vitro pacemaking assay comprising SANLCMs aggregates and a VLCM monolayer can be used to test whether a candidate drug can disrupt the ability of SANLCMs to pace a VLCM monolayer. For example, VLCM cells are placed on MEAs and cultured until formation of an electrical integrated monolayer. Aggregates of SANLCMs are then placed on the VLCM monolayer and following electrical integration of SANLCM aggregates and VLCM monolayer, field potentials are recorded.

In an embodiment, the in-vitro pacemaking assay is used as a safety pharmacology screen.

In an embodiment, the candidate drug is for treating diseases affecting the SAN, including Sick Sinus Syndrome (SSS), bradycardia, tachycardia, sinus node arrest/block caused by aging (mostly fibrosis of the sinus node) or genetic disorder.

Genetic disorders causing SSS described include for example SCN5a (Gene ID: 6331) sodium channel mutations, HCN4 (Gene ID:10021) mutation, Cx40 (Gene ID: 2702) mutation, Myh6 (Gene ID:4624) mutations and Ankyrin-B (Gene ID: 287) mutations.

Disease modeling can be accomplished by preparing SANLCM from a subject with a disease condition or disorder affecting pacemaker cells.

Accordingly in an embodiment, the hPSCs are induced hPSCs prepared from a subject with a suspected disease, condition or disorder affecting pacemaker cells or VLCMs cells. The cells can be used to test drug candidates and/or for molecular, genomic, proteomic, physiological (including action potentials, ion currents) or other analyses.

In an embodiment, the use or method is for in vivo pacemaking. As shown in Example 2, the isolated population of cardiomyocytes enriched for SANLCMs and/or the substantially pure population of SANLCMs can be used for in vivo transplantation to confer pacemaker capacity.

In an embodiment, the use or method is for treatments requiring populations of cells free of pacemaker cells including for example ventricular cell transplantation for remuscularization after myocardial infarction.

The ability of the cells to function as an in vivo pacemaker was tested by transplanting cell aggregates into the apex of a rat heart. The heart beat was first decreased pharmacologically to resemble that of a human heart beat. It was shown ex-vivo, that rat hearts receiving the SANLCM transplant displayed a significantly faster ventricular ectopic rhythm after induction of atrioventricular (AV) block.

Cardiomyocytes for example enriched for SANLCMs or SANLCMs can be introduced to the heart by a minimal invasive method using a catheter-based approach. The catheter can be inserted via the femoral, subclavian, jugular or axillary vein by endocardial transplantation approach into the ventricle, atria or SAN region. Alternatively, the cells can be transplanted into the ventricle, atria or SAN region by epicardial approach using a needle inserted through the chest. In both approaches, Fluoroscopy (X-Ray based method) or 3D Mapping can be used to guide the catheter/needle to the intended injection site.

The ability of the cells to function as a pacemaker was also assessed ex vivo. Ten days post-transplantation, hearts were harvested and electrocardiographic recordings and fluorescent voltage imaging were performed, as shown in Example 2. Optical mapping confirmed that the new ectopic rhythm was initiated from the SANLCM transplantation site.

Accordingly a further aspect includes a method of treating a subject in need thereof comprising administering to the subject a population of cardiomyocytes enriched for SANLCM or SANLCM to the subject, a cell or composition described herein, or a biological pacemaker (e.g. 3D and/or comprising endothelial cells, mesenchymal stem cells and/or smooth muscle cells and optionally extracellular matrices that are used to form 3D tissues).

Similarly, NKX2-5$^+$ cardiomyocyte cultures that are free of SANLCMs can be used in cell therapy approaches that require populations free of pacemaker cells, for example for ventricular cell transplantation for remuscularization after myocardial infarction.

Accordingly a further aspect includes a method of treating a subject in need thereof comprising administering to the subject a population of cardiomyocytes substantially devoid of SANLCM to the subject, a cell or composition described herein.

Uses of the cell populations for treating a subject in need thereof as described herein are also envisioned.

Administration to a subject of a population of cardiomyocytes, including for example cardiomyocytes enriched for SANLCMs or consisting of SANLCMs or substantially devoid of SANLCMs can be done for example by the use of ESC-derived (HLA class matched, not necessarily patient specific) cells or for example by the use of iPSC-derived (patients' own cells) SANLCMs or VLCMs. The cells can be injected via a catheter (see above) as single cells or small aggregates into the left or right ventricular wall or apex of the heart.

In addition, prior to in vivo use, it is possible to confirm the cardiomyocyte subtype and/or to ensure the desirable amount of SANLCMs or VLCMs have been obtained.

As described above, this can be accomplished by taking an aliquot of the cell sample and testing the sample for SAN markers (e.g. Shox2, Tbx18, Tbx3, ISL1) or other markers or their absence including NKX2-5 expression using for example an antibody specific to NKX2-5 such as rabbit anti-human NKX2-5. This protocol can be applied as a quality control for the SANLCM differentiation prior to in vivo use of the cells.

For example, a small aliquot of the cells can be taken to test for an acceptable number or density of SANLCMs.

A further aspect is a composition comprising an isolated population of cardiomyocytes, for example enriched for or substantially devoid of SANLCMs and/or isolated SANLCMs or VLCMs and a pharmaceutically acceptable carrier. In an embodiment, the isolated population comprises cells comprising a NKX2-5 reporter such as NKX2-5 GFP reporter. In an embodiment, the isolated population is a clonal population derived from an ESC cell line or an iPSC.

As indicated by their names the SANLCM are SAN like CM and the VLCM are V like CM. They may represent a fetal development stage and therefore may have one or more differences than adult SANCM and VCM. SANLCM for example may beat faster—for example around 120 bpm, or around 150 bpm—than an adult SAN pacemaker cell which beats around 60-100 bpm. In an embodiment, the VLCM described herein may express a lower level of Kir2.1 ion-channel, higher level of HCN4, HCN2, and/or may have immature calcium handling properties compared to adult ventricular cardiomyocytes.

Yet a further aspect is a biological pacemaker comprising an isolated population of cardiomyocytes enriched for SAN-LCMs and/or isolated SANLCMs and a pharmaceutically acceptable carrier.

In the engineering of a biological pacemaker, three dimensional (3D) tissues can be used to ensure vascularization and potential innervation of the grafted cells.

In an embodiment, the biological pacemaker further comprises endothelial cells, mesenchymal stem cells and/or smooth muscle cells and optionally extracellular matrices that are used to form 3D tissues.

For example, Tolloch et al.[33] used human embryonic stem cells and human induced pluripotent stem cell-derived cardiomyocytes and developed a collagen-based, bio-engineered human 3D cardiac tissue construct in a self-organizing co-culture with endothelial and stromal cells.

In an embodiment, markers herein disclosed such as ventricular specific markers (e.g. MYL2 and IRX4) and SAN specific markers (e.g. TBX18, TBX3, SHOX2 and ISL1) can be detected using any one of the primer sequences in Table 3.

As mentioned herein VLCM populations can be produced by activating FGF signaling to generate cultures of NKX2-5$^{pos}$ cardiomyocytes. In some methods, the methods for producing and/or isolating VLCM comprise using a reporter construct. For example, an embodiment provides a method of isolating ventricular-like cardiomyocytes from a population of cardiomyocytes comprising a) producing a population of cardiomyocytes from PSCs comprising a NKX2-5 reporter construct as described herein and b) selecting NKX2-5 positive cardiomyocytes and/or removing NKX2-5 negative cardiomyocytes.

Methods of producing VLCM cells are known and described for example in the Witty A. D. et al. Generation of the epicardial lineage from human pluripotent stem cells. *Nature Biotechnology, doi:*10.1038/nbt.3002 (2014) which is incorporated herein by reference. The method described in Witty et al can for example be enhanced by addition of a FGF component during the cardiac induction phase It is demonstrated herein that VLCM cells can be isolated and/or removed from a population of cardiomyocytes according to NXK2-5 reporter expression.

For example, cells comprising a NKX2-5 reporter construct that are positive for reporter protein expression can be isolated or depleted from a population of cardiomyocytes generated according to a method described herein.

A further aspect includes the use of an isolated population of cardiomyocytes enriched for VLCMs and/or a population of VLCMs depleted of NKX2-5 expressing cells for in vivo transplanting in a subject.

Figure 11:
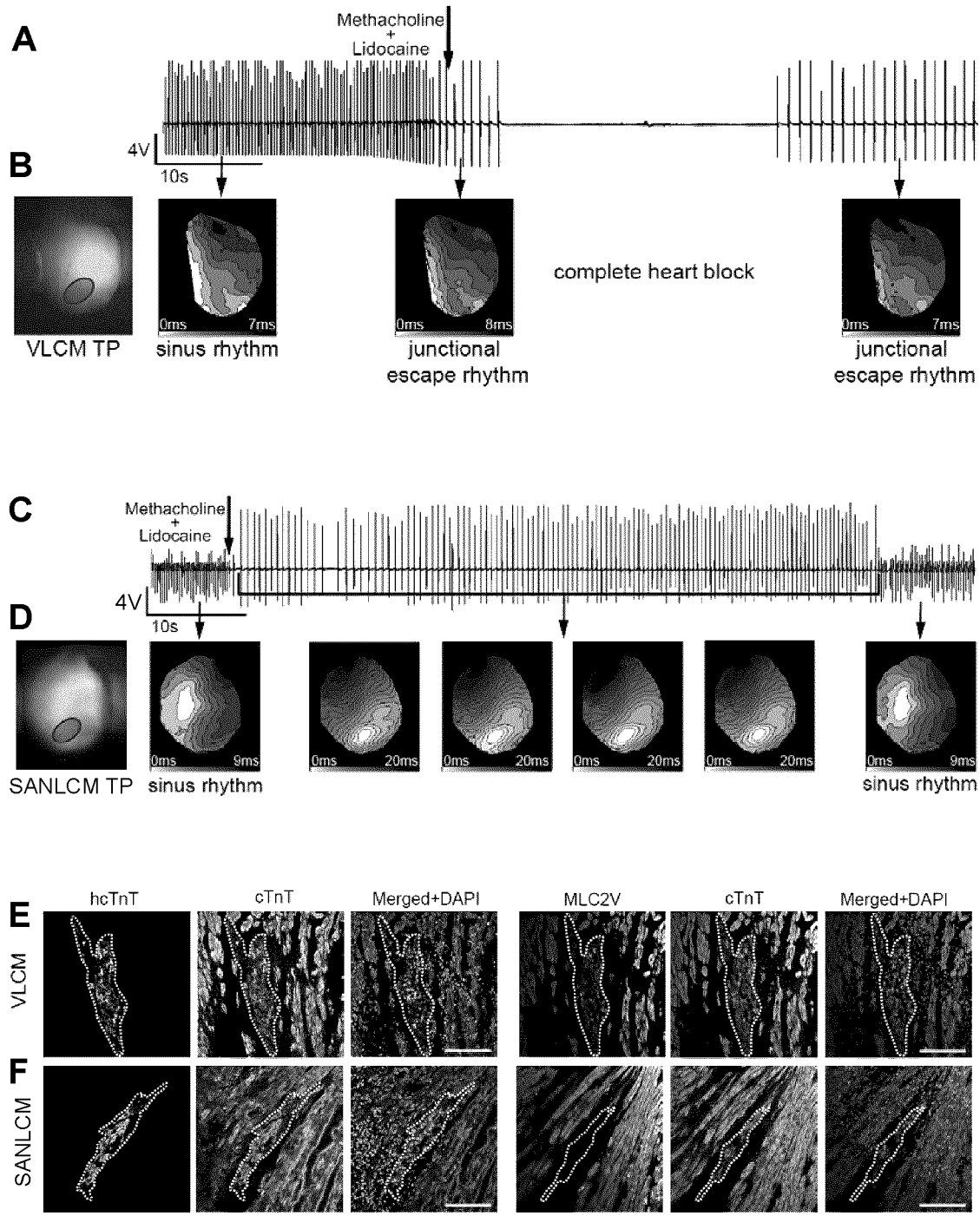
FIG. 11. SANLCM can act as biological pacemaker in-vivo. A, B, Example of rat heart with VLCM transplant (1-2×10⁶ cells) harvested 14 days post-transplantation. Original ECG traces before and after the application of Methacholine+Lidocaine in the Langendorff isolated heart model (A). Picture of rat heart with indicated transplantation site (ellipse) and whole heart optical mapping of the electric activity corresponding to the ECG trace (B). C,D, Example of rat heart with SANLCM transplant (1-2×10⁶ cells) harvested 14 days post-transplantation. Original ECG traces before and after the application of Methacholine+Lidocaine in the Langendorff isolated heart model (C). Picture of rat heart with indicated transplantation site (ellipse) and whole heart optical mapping of the electric activity corresponding to the ECG trace (D). Of note, the initiation site of the ectopic beats correlates with the transplantation site. E,F, Immunostaining of cryosections of rat hearts with VLCM (E) and SANLCM (F) transplant. A human specific cTnT (hcTnT) antibody was used to identify the human transplant. Sections were counterstained with cTNT to mark rat and human cardiomyocytes. Sections were stained for MLC2V to distinguish the VLCM (MLC2V⁺) and the SANLP (MLC2V⁻) transplant. DAPI was used to mark cell nuclei. Dashed line indicates the human transplant. Scale bars represent 200 µm. TP, transplant.

It is demonstrated herein that VLCMs have reduced pacemaker capacity (FIG. 11A). VLCMs prepared from hPSCs depleted of SANLCMs may have some benefits. For example, depleting SANLCMs could reduce arrhythmias upon transplantation of VLMCs, for example for ventricular cell transplantation for remuscularization after myocardial infarction.

The above disclosure generally describes the present application. A more complete understanding can be obtained by reference to the following specific examples. These examples are described solely for the purpose of illustration and are not intended to limit the scope of the application. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Example 1

Methods
hPSC Maintenance and Differentiation

Human pluripotent stem cell lines (Hes3 NKX2-5:GFP)[10] H7 (HESC line approved by NIH registration number 0061[32] and MSC-iPS1[11] were cultured as described[12]. For differentiation into the cardiac lineage the established protocol[6] was used with the following modifications (FIG. 1A). 80% confluent hPSCs cultures were dissociated into single cells, suspended in StemPro-34 Media containing 1 ng/ml BMP4 and 10 µM ROCK inhibitor and incubated for 18 h on an orbital shaker to generate embryoid bodies (EBs). The next day (day 1 of differentiation) the EBs were transferred to mesoderm induction media: StemPro-34 containing 10 ng/ml BMP4, 6 ng/ml ActivinA, 5 ng/ml bFGF. At day 3 of differentiation the EBs were washed once using IMDM and suspended in cardiac induction media: StemPro-34 containing 0.5 µM IWP2, 10 ng/ml VEGF, and optionally 5.4 µM SB-431542 (SB, Activin/Nodal/TGFβ inhibitor). At day 5 of differentiation EBs were switched to basic media: Stempro containing 5 ng/ml VEGF. Media was supplemented with VEGF until day 12 of differentiation and changed every 4 days. All cytokines were purchased from R&D systems if not indicated otherwise. EBs were cultured under low oxygen conditions 5% $CO_2$, 5% $O_2$, 90% $N_2$ until day 12 and at 5% $CO_2$, normal air conditions for the rest of the culture period.

Pacemaker (SANLCM) Optimized Protocol

EBs were dissociated into single cells at the mesoderm stage (day 3 of differentiation) using TrypLE (Life Technologies) with the rational to ensure efficient cytokine supply to each cell. Cells were placed into 96 well low cluster plates at 80,000 cells/well with the indicated cytokines and 5 µM ROCK inhibitor for re-aggregation into EBs (FIG. 2A). At day 5 of differentiation EBs were transferred to 24 well low cluster plates and continued to be cultured in basic media as described above.

For efficient specification of SANLCM pacemaker, mesoderm was induced with the 3B/2A condition (3 ng/ml BMP4, 2 ng/ml ACTA) at day 1 of differentiation. At day 3 EBs were dissociated as described above and treated with 2.5 ng/ml BMP4 and 0.5 µM RA in addition to standard cardiac induction media.

For the generation of SANLCM cultures free of NKX2-5$^+$ cardiomyocytes mesoderm was induced with the 3B/2A condition (3 ng/ml BMP4, 2 ng/ml ACTA) at day 1 of differentiation. For this protocol EBs were kept intact and treated at day 3 with 2.5 ng/ml BMP4, 0.5 µM RA and 960 nM FGF inhibitor (PD 173074, Tocris) at day 3 or day 4 in addition to standard cardiac induction media.

Flow Cytometry and Cell Sorting

For the dissociation of day 3-day 12 EBs TrypLE was used. Day 12-30 EBs were incubated in HANKs buffer containing 1 mg/ml Collagenes type 2 (Worthington) with gentle shaking over night at room temperature, prior to TypLE dissociation. Cells were stained at a concentration of 5×10$^6$ cells/ml with anti-PDGFRα-PE (1:20) anti-KDR-APC (1:10), (R&D Systems), anti-SIRPA-PeCy (clone SE5A5, 1:1000, Biolegend), anti-CD90-APC (BD), anti-cardiac isoform of cTNT (clone 13-11; 1:2000, Thermo Fischer), rabbit anti-human NKX2-5 (1:800, Cell Signaling Technology), goat anti-mouse IgG APC (1:250, BD), goat anti-mouse IgG PE (1:200, Jackson ImmunoResearch), donkey anti-rabbit IgG A647 Life Technologies). For cell-surface markers staining was carried out in PBS containing 5% FCS. For intra-cellular staining cells were fixed for 10 min at 4° C. with 4% PFA and stained in PBS containing 5% FCS and 0.5% saponin (cTNT) or 0.3% TritonX (NKX2-5). Stained cells were analyzed using the LSR II Flow cytometer (BD). For cell sorting the cells were kept in IMDM containing 5% FCS and sorted at a concentration of 10$^6$ cell/ml using MoFlo (BD) and Influx (BD) sorter. For sorting of PFA-fixed cells for subsequent RNA isolation the staining buffers and PBS for cell collection were supplemented with 5 mM DTT and 100 U/ml RNaseOUT (Life Technologies). All buffer components were RNAse free and samples were strictly kept on ice and sorted within 3 h from PFA-fixation. Data were analyzed using FlowJo software (Tree Star).

Immunocytochemistry

Cells were fixed with 4% PFA for 10 min at 4° C. and permeabilized using 0.3% Triton X, 200 mM Glycerin for 20 min at RT. Samples were blocked for 30 min at room temperature in blocking buffer (BB): 10% donkey serum, 2% BSA, 0.1% Triton X. The following primary antibodies were incubated in BB over night at 4° C.: anti-cardiac isoform of cTNT (clone 13-11; 1:100, Thermo Fischer), rabbit anti-human MLC2v (1:100), rabbit anti-human SHOX2 (1:200), (Abcam), rabbit anti-human TBX3 (1:100), goat anti-human Tbx18 (1:50), (Santa Cruz). Respective secondary antibodies were incubated for 30 min at RT: donkey anti-mouse IgG A647 (1:400), donkey anti-rabbit IgG A467 (1:400), (Life Technologies), goat anti-mouse IgG Cy3 (1:400), donkey anti-rabbit IgG Cy3 (1:800), donkey anti-goat IgG Cy3 (1:800), (Jackson ImmunoResearch). DAPI was used to counterstain cell nuclei and slides were mounted using Fluorescent Mounting Medium (Dako). The Olympus FluoView 1000 Laser Scanning Confocal Microscope and the FV10-software were used for imaging.

For the quantification of DAPI and TBX18 positive cell nuclei the IMAGE J software plugin ICTN was used. For each condition three random taken pictures (FIG. 3F) of three independent experiments were analyzed.

Quantitative Real-Time PCR

Total RNA was isolated using the RNAqueous-micro Kit (Ambion) followed by a DNase digestion step (Ambion). For RNA isolation from PFA-fixed cells the RecoverAll Kit (Ambion) was used. 500 ng to 1 μg of RNA was reverse transcribed into cDNA using random hexamers and Oligo (dT) primers with Superscript III Reverse Transcriptase (life technologies). QPCRs were performed on the EP RealPlex MasterCycler (Eppendorf) using the QuntiFast SYBR Green PCR Kit (Qiagen) according to the manufacturer's instructions. A 10-fold dilution series of human genomic DNA standards ranging from 25 ng/μl to 2.5 pg/μl was used to evaluate the efficiency of the PCR and calculate the copy number of each gene relative to the house keeping gene TBP as described previously[13]. Primer sequences are listed in Table 3. Human fetal heart tissue gestation stage 17 was purchased from Novogenix Laboratories. After dissecting ventricular, sinoatrial node and atrioventricular node tissue RNA was isolated using the Trizol method (Life Technologies) and treated with DNase (Ambion).

Patch Clamp

Action potentials and membrane currents were measured with standard current- and voltage-clamp techniques using axopatch amplifier. For data acquisition and analysis pCLAMP software (Molecular Devices) was used. Borosilicate glass microelectrodes had tip resistances of 2-5 MΩ when filled with pipette solution. Series resistance and cell capacitance were compensated up to 70%. Spontaneous action potentials, funny current ($I_f$) and inward rectifier potassium currents currents ($IK_r$) were recorded at 37° C. using the perforated patch method (nystatin)[14] with the following bath solution (mM): NaCl 124, KCl 5.4, CaCl$_2$ 1.2, MgCl$_2$ 1, and glucose 5, Hepes 10 (pH 7.4, adjusted with NaOH). The pipette solution consisted of (mM): NaCl 5, KCl 10, potassium gluconate 130, MgCl$_2$ 1, and Hepes 10 (pH 7.4, adjusted with KOH). Sodium currents ($I_{Na}$) were recorded at 25° C. using the whole cell ruptured patch method in calcium free bath solution containing low Na$^+$ to reduce current amplitude for better voltage control (mM): NaCl 30, TEA-Cl 115, CaCl$_2$ 0.01, MgCl$_2$ 1, and glucose 5, Hepes 10 (pH 7.4, adjusted with NaOH). The pipette solution consisted of (mM): Cs-aspartate 112, CsCl 20, MgCl$_2$ 1, Mg-ATP 5, Cs-EGTA 10, Hepes 10 (pH 7.4, adjusted with CsOH). The voltage protocols to elicit the individual currents are shown in the respective figures.

Multielectrode Array Experiments

For in-vitro pacing experiments 1×10$^6$ VLCM were plated on matrigel-coated Multielectrode arrays (MEA) and cultured for 5-7 days to form electrical integrated monolayers. Aggregates (3×10$^4$ cells) of SANLCMs or VLCMs (control) labeled with Tetramethylrhodamine methyl ester (TMRM) were placed at a specific site on these established VLCM monolayers. Electric signals (Field potentials) were recorded in basic media at 37° C. using the Multichannel systems amplifier, heating unit and Cardio-2D software. Greyscale-Maps of electric signal propagation were generated using the Cardio-2D+ software (multichannelsystems).

Statistics

Data presented as means±standard error of the mean. Statistical analyses were performed using Student's T-test. Results were considered to be significant at p<0.05 (*/#) and very significant at p<0.01 (**/##).

Results

To generate hESC-derived cardiovascular cells a developmentally staged protocol[6,15] that involves the formation of a primitive streak-like population (days 2-3) expressing T(BRACHYURY) followed by the induction of cardiac mesoderm characterized by the expression of MESP1 and PDGFRα/KDR (days 3-4) was used. This PDGFRα$^+$ KDR$^+$ mesoderm gives rise to 60-90% cTNT$^+$ cardiomyocytes (day 20) (FIG. 1A and FIG. 5A, B). With this protocol, expression of transcription factors involved in the development of the sinoatrial node (SAN)[16] including TBX18, SHOX2 and TBX3 was upregulated, between days 3 and 8 of differentiation, suggesting that pacemaker cells are being specified under these conditions (FIG. 1B). As studies in both mouse and human indicate that SAN cells derive from a progenitor that does not express the pan-cardiomyocyte transcription factor NKX2-5[17-19], it was hypothesized that it would be possible to distinguish the hPSC-derived pacemaker cells from other cardiomyocytes based on expression of NKX2-5. To test this, the cultures were monitored for the presence of NKX2-5$^+$/NKX2-5$^-$ cardiomyocytes, using the HES3 NKX2-5:GFP reporter line[10] in combination with the pan-cardiomyocyte surface marker SIRPA[13]. The first NKX2-5:

GFP$^+$SIRPA$^+$ cells were generated within 6 days of differentiation and the size of the population increased to represent 60±3% of the culture by day 16 (FIG. 1C). Also, a distinct NKX2-5:GFP$^-$SIRPA$^+$ population was detected by day 16. The cardiomyocyte nature of these cells was confirmed by cTNT staining which revealed a large (63±8%) NKX2-5:GFP$^+$cTNT$^+$ population and a small (6±2%) NKX2-5:GFP$^-$cTNT$^+$ population.

To determine if the NKX2-5:GFP$^-$ cardiomyocytes represent SAN pacemaker cells, the NKX2-5:GFP$^+$SIRPA$^+$ (NKX2-5$^+$) and the NKX2-5:GFP$^-$SIRPA$^+$ (NKX2-5$^-$) fractions from day 20 populations were isolated. The mesenchymal marker CD90 was included to deplete non-myocytes from the NKX2-5:GFP$^-$ fraction (FIG. 1D and FIG. 5C). Consistent with a pacemaker phenotype, aggregates derived from the NKX2-5$^-$ population had significantly faster beating rates (83±4 bpm) than the NKX2-5$^+$ aggregates (40±3 bpm) (FIG. 1E).

Molecular analyses revealed that the NKX2-5$^+$ and NKX2-5$^-$ populations expressed similar levels of cTNT indicating comparable cardiomyocyte content (FIG. 1F). NKX2-5$^-$ cells expressed significantly less NKX2-5, than the NKX2-5$^+$ cells, consistent with the sorting strategy. The ventricular markers MYL2 and IRX4 were expressed at higher levels in NKX2-5$^+$ cells than in NKX2-5$^-$ cells, indicating that the NKX2-5$^+$ population contains ventricular-like cardiomyocytes. Genes encoding pacemaker-specific transcription factors including TBX18, TBX3, SHOX2 and ISL1 showed the opposite pattern and were express at significantly higher levels in NKX2-5$^-$ cells (FIG. 1G). Fetal heart tissues included confirmed that the SAN markers TBX18, SHOX2 and ISL1 established in the mouse heart[16] were also expressed at higher levels in human SAN tissue (F-SAN) compared to ventricular tissue (F-V) and secondary pacemaker atrioventricular node tissue (F-AVN). Accordingly, markers that define the AVN pacemaker including TBX2 and MSX2[20,21] were expressed at highest levels in the AVN tissue (FIG. 1H). Expression of theses AVN-specific genes was not upregulated in the hESC-derived NKX2-5$^-$ population indicating that it does not contain AVN cells. The pacemaker ion channels genes, HCN4, HCN1 and KCNJ3 were expressed at higher levels in NKX2-5$^-$ cells compared to NKX2-5$^+$ cells (FIG. 1I), while the sodium channel SCN5a showed the opposite pattern. These expression profiles were validated in populations isolated at day 20 by intracellular FACS based on cTNT and NKX2-5 expression (NKX2-5$^+$/cTNT$^+$ and NKX2-5/cTNT$^+$) (FIG. 5D-H).

Figure 6:
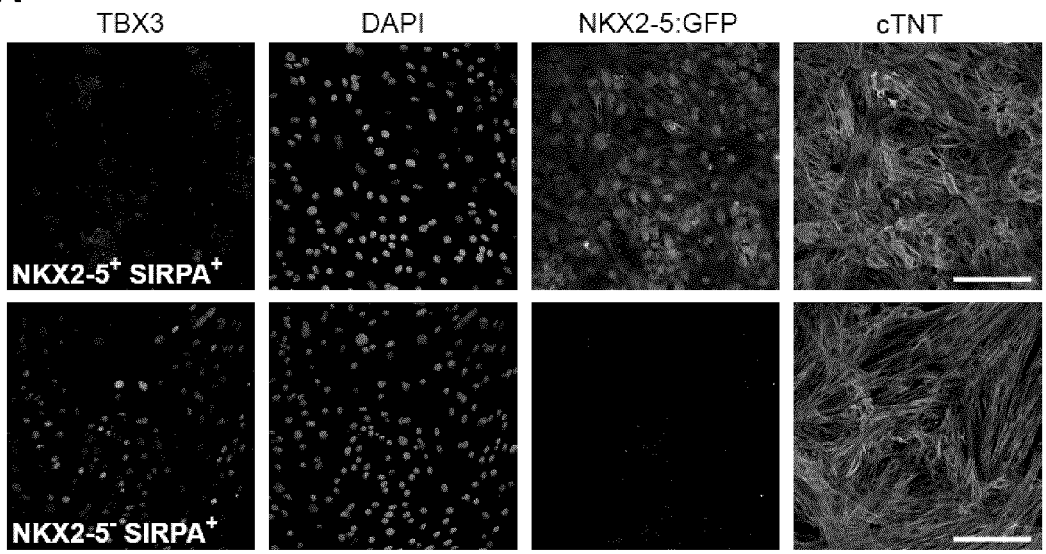
FIG. 6. A, Immunostaining for pacemaker transcription factor TBX3 in NKX2-5$^+$SIRPA$^+$ and NKX2-5$^-$ SIRPA$^+$ sorted cells from day 20 cultures. Cells were counterstained with cTNT to mark cardiomyocytes and DAPI to mark cell nuclei. B, Immunostaining for cTNT in NKX2-5$^+$SIRPA$^+$ and NKX2-5$^-$ SIRPA$^+$ sorted cells at 30 days post-sorting. The NKX2-5:GFP transgene expression was visualized to proof that NKX2-5$^-$ sorted cardiomyocytes stay NKX2-5 negative for up to 30 days after the sort. Scale bars represent 100 µm. C, Representative FACS plot of NKX2-5$^+$SIRPA$^+$ and NKX2-5$^-$ SIRPA$^+$ sorted cells for NKX2-5:GFP and cTNT at 30 days post-sorting.
Figure 6:
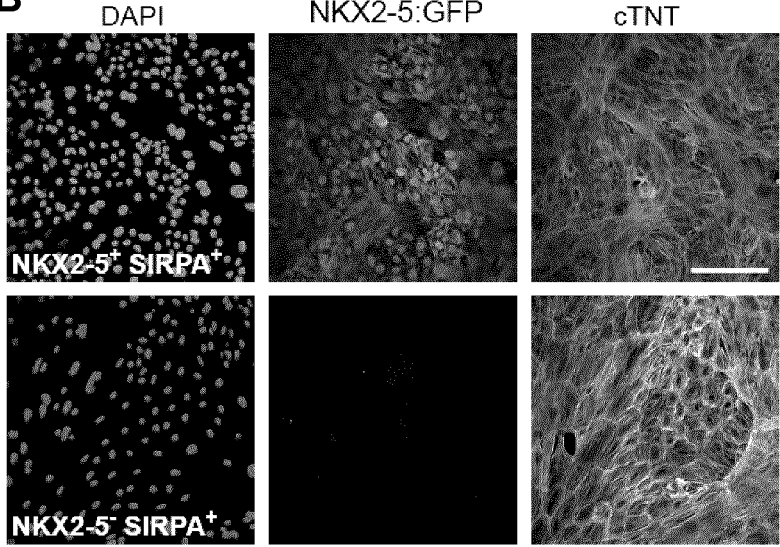
Figure 6:
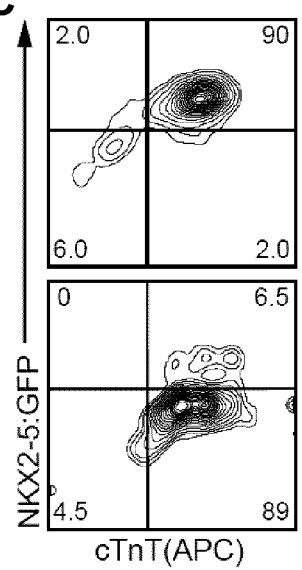

Immunostaining confirmed the findings from the molecular studies and showed that NKX2-5$^+$ but not NKX2-5$^-$ myocytes expressed the ventricular protein MLC2V as well as NKX2-5 (FIG. 1J). SHOX2 and TBX3 showed the reverse pattern and were detected at much higher levels in NKX2-5$^-$ cells. (FIG. 1K and FIG. 6A). When maintained in culture for up to 30 days only a small proportion (5±1%) of the NKX2-5$^-$ fraction upregulated expression of NKX2-5: GFP, indicating that the majority of these cells represent a distinct sub-population of cardiomyocytes rather than immature progenitors that have not initiated NKX2-5 expression (FIG. 6B, C).

Figure 7:
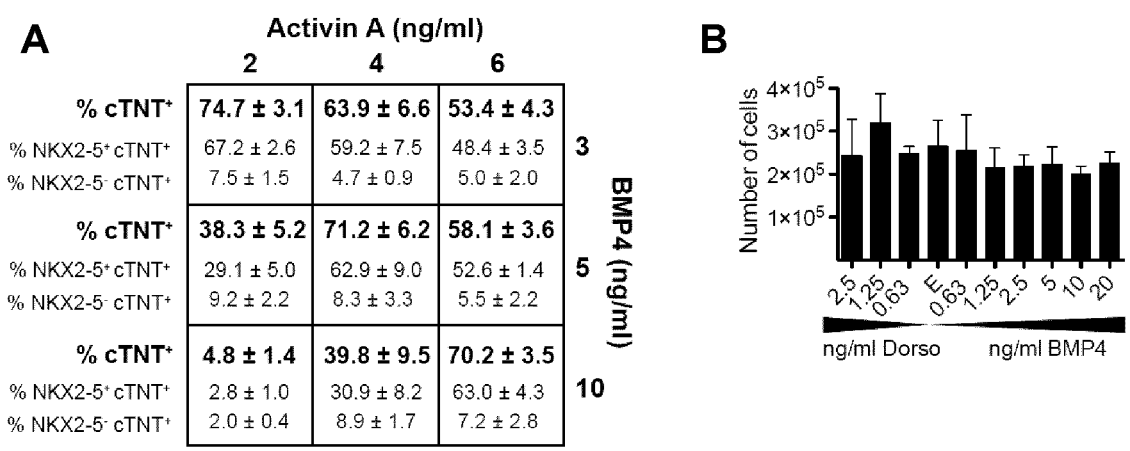
FIG. 7. A, Analysis of total cTNT and NKX2-5$^+$/NKX2-5$^-$ proportion of cTNT$^+$ cells after induction of mesoderm with indicated amounts of BMP and ACTA at day 1 of differentiation. B, Total number of cells at day 20 of differentiation after treatment with different concentrations of either Dorsomorphin (Dorso) or BMP4 (n=4). Error bars show s.e.m.

Although the existing protocol promoted the development of SANLCMs, the efficiency of generating these cells was low (5-9%). Therefore, a hESC-differentiation model was used to gain a better understanding of SAN lineage development. For this the effect of manipulating signaling pathways was investigated at two distinct stages; mesoderm induction (day 1-3) and cardiovascular specification (day 3-5). For the mesoderm induction step, the concentrations of BMP4 and ACTA was varied as these signaling pathways regulate the development of cardiovascular mesoderm[6]. Efficient cardiomyocyte differentiation (70-75%) was achieved with three different combinations of these pathway agonists; standard concentrations, 10B/6A (10 ng/ml BMP4, 6 ng/ml ACTA) and lower concentrations including 5B/4A (5 ng/ml BMP4, 4 ng/ml ACTA) and 3B/2A (3 ng/ml BMP4, 2 ng/ml ACTA). (FIG. 7A). None of these combinations led to an increase in the proportion of SANLCMs (7±3% at 10B/6A vs 8±3% at 5B/4A and 8±2% at 3B/2A).

Given that the epicardial lineage, a cell type developing from a common progenitor with SAN pacemakers is specified from cardiovascular mesoderm by BMP4 signaling[22], it was next tested if manipulating the BMP4 pathway would impact the development of SANLCMs from the three different mesoderms (FIG. 2A). As reported previously[22], blocking BMP signaling (dorsomorphin) or exposure to high levels of BMP4 (10-20 ng/ml) between day 3-5 of differentiation resulted in a significant reduction of total cardiomyocytes (FIG. 2B-D and FIG. 7B). Importantly, lower levels of BMP4 (1.25-5 ng/ml) led to a notable increase in the proportion of SANLCMs up to 35±1%. Under these conditions, the NKX-2-5:GFP$^-$ SANLCMs could be easily resolved as a distinct population, based on cTNT/SIRPA expression (FIG. 2E). The effect was greatest in the mesoderm induced with 3B/2A (35±1% vs 15±2% at 10B/6A vs 21±1% at 5B/4A), suggesting that SANLCMs derive from a distinct subpopulation of mesoderm that is induced with low concentration of BMP4 and ACTA. The increase in the proportion of SANLCMs was most pronounced if BMP4 was added between days 3 and 4 of differentiation (FIG. 2F). Addition of BMP4 for longer periods of time did not increase the proportion of SANLCMs, whereas activation of the pathway earlier, (days 2-3, 2-4) or later (days 4-5, 4-6) resulted in a reduction in the frequency of SANLCMs. These observations highlight the dynamic nature of lineage specification in hPSC differentiations and the importance of manipulating signaling pathways at the appropriate developmental stage.

Given that the SAN derives from a TBX18$^+$ progenitor, TBX18 expression during BMP4-induced SANLCM specification was monitored. Consistent with the initial analyses (FIG. 1B), TBX18 expression was upregulated between days 4 and 6 of differentiation and treatment with BMP4 significantly up-regulated TBX18 (FIG. 2G). Immunostaining confirmed the expression studies and showed that the BMP4-induced population contained significantly more TBX18$^+$ cells than the control population (FIG. 2H, I). Notably the number of TBX18$^+$ cells at day 6 (38±2%) correlated with the number of SANLCMs at day 20 (35±1%), a finding supporting the interpretation that SAN-LCMs derived from a TBX18$^+$ progenitor.

Retinoic acid (RA) signaling is known to play a pivotal role in the generation of atrial cardiomyocytes that derive from progenitors positioned in the posterior region of the heart tube[23,24]. As the SAN also develops from the posterior heart tube, it was next asked if RA signaling impacts the development of SANLCMs. Addition of RA (500 nM e.g. about 150 ng/mL) at day 2 blocked the generation of cardiomyocytes (FIG. 3A). When added at later times (days 3 to 12), RA had no effect on the generation of total cardiomyocytes and SANLCM frequency. Although RA did not affect the efficiency of SANLCM development, qRT-PCR analyses of the isolated NKX2-5$^-$SIRPA$^+$ fraction revealed a significant upregulation of the posterior cardiomyocyte marker TBX5 and the SAN marker SHOX2, when RA was added to the cultures between days 3 to 5 (FIG. 3B).

Figure 8:
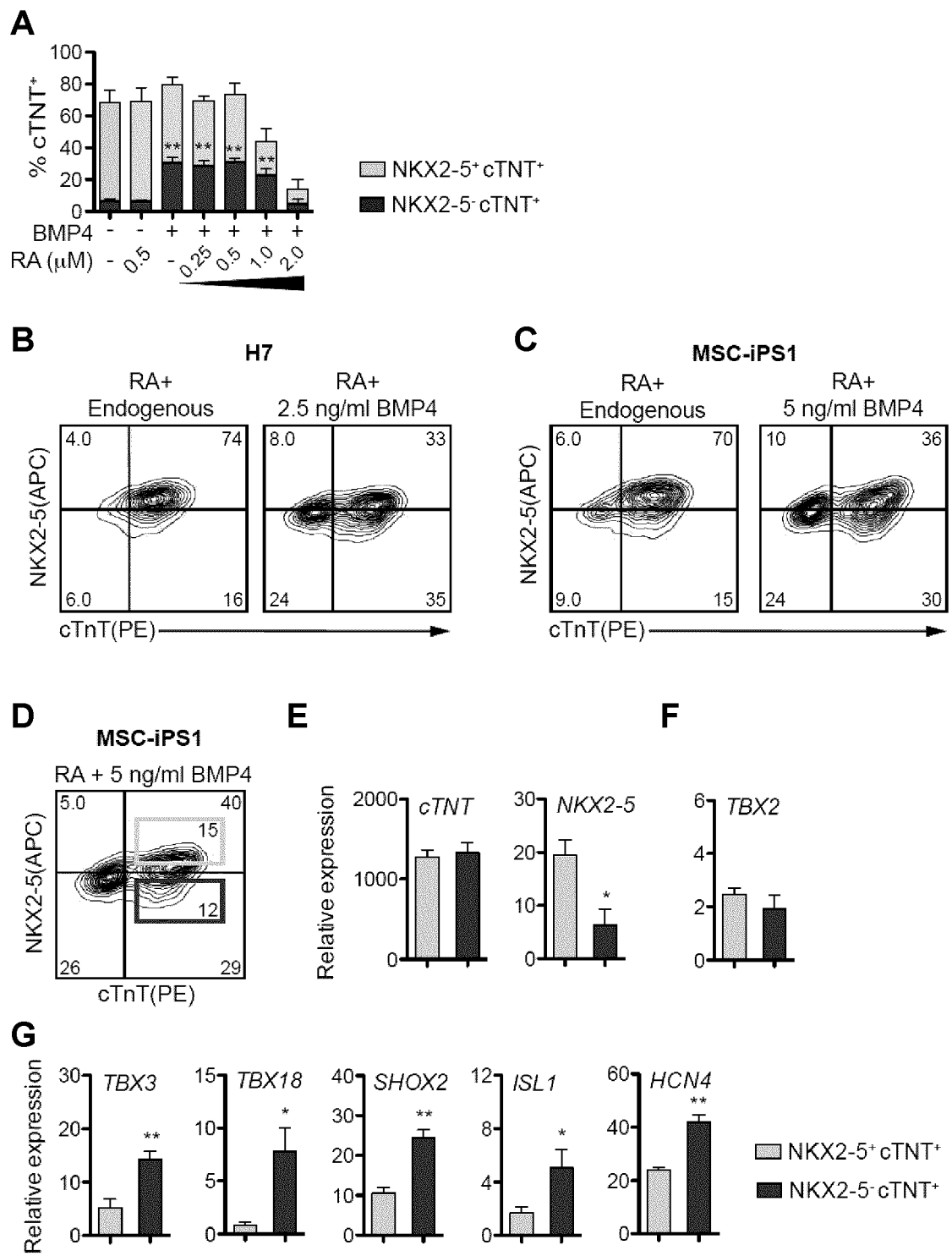
FIG. 8. A, Summary of day 20 FACS results for NKX2-5 and cTNT after retinoic acid (RA) (day 3), BMP4 (day 3-5) and combined RA+BMP4 treatment. T-test: **P<0.01 vs NKX2-5⁻ cTNT⁺ cells in untreated control condition (n=4). B,C, Representative FACS plots for NKX2-5 and cTNT staining in day 20 cultures of the H7 hESC line (B) and the MSC-iPS1 iPSC line (c) differentiated with 500 nM RA at day 3 and the indicated BMP4 concentrations from day 3-5. D, Representative FACS plot for sorting strategy of NKX2-5⁺cTNT⁺ and NKX2-5⁻cTNT⁺ cells. Due to the lack of a SANLCM specific surface marker MSC-iPS1 cultures were PFA fixed at day 20 and stained for NKX2-5 and cTNT. E-G, Q-PCR analysis of: sorting markers (E) AVN pacemaker marker (F) SAN pacemaker marker (G). Expression relative to the housekeeping gene TBP. T-test: *P<0.05, **P<0.01 vs NKX2-5⁺cTNT⁺ cells (n=4). Error bars show s.e.m.

Importantly, addition of RA (day 3) did not impact the BMP4-induced increase in SANLCM specification (FIG. 3c and FIG. 8A) nor did it alter the levels of TBX18 expression (FIG. 3D). RA treatment alone and in combination with BMP4 increased the expression of TBX5, SHOX2 and ISL1 and further decreased the expression of MYL2 (FIG. 3E). Combined RA/BMP4 signaling significantly increased the expression of the pacemaker ion channel genes HCN4 and HCN1 but not the AVN genes TBX2 and MSX2 (FIG. 3F). The improved RA/BMP-induced pacemaker expression profile was associated with a significant increase in the beating rate of the cells (138±7 bpm) (FIG. 3G). These rates are within the range of the human fetal heartbeat which is at 120-160 bpm[25].

Taken together, these findings support a model in which the SAN lineage is specified from an appropriately induced mesoderm population (3B/2A) by BMP signaling through a TBX18$^+$ progenitor. RA signaling by contrast does not affect the efficiency of SAN lineage specification but rather enhances the pacemaker phenotype in SAN progenitors (FIG. 3H). Using this strategy SANLCM could be generated from the H7 hESC line and the MSC-iPS1 hiPSC line (FIG. 8B-G).

Figure 9:
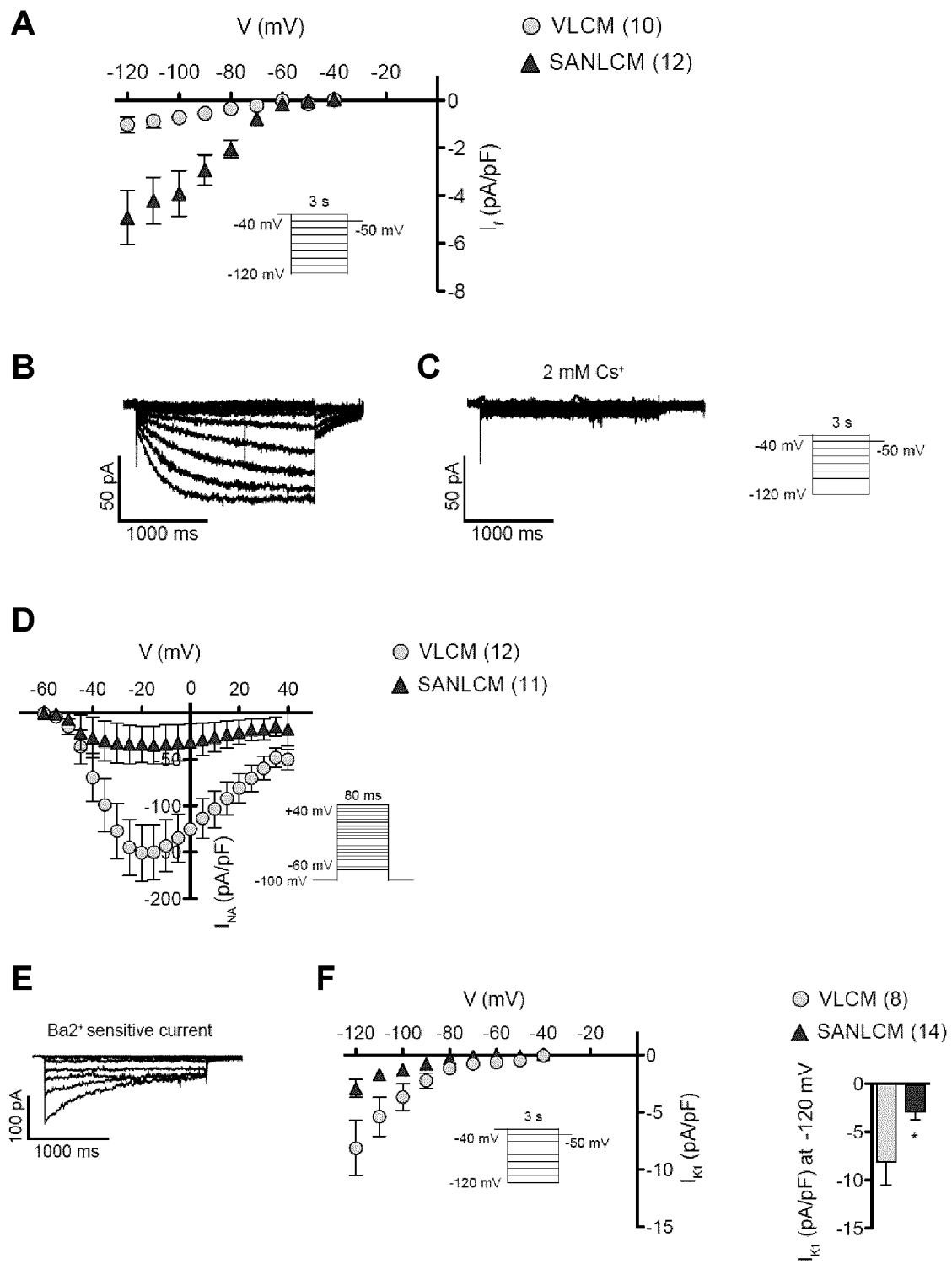
FIG. 9. A, Current-voltage relationship for pacemaker funny current density ($I_f$) in SANLCM and VLCM. Inset: voltage protocol, from a holding potential of −40 mV currents were elicited by 3 s voltage steps of −10 mV down to −120 mV. Current densities were measured by subtraction of the instantaneous current (t=0) from the current at the end of the 3 sec voltage step. B,C, Original pacemaker funny current traces at different membrane potentials in Tyrode's solution (B) and blocked by the application of 2 mM Cesium (Cs⁺) (C). Inset: voltage protocol, from a holding potential of −40 mV currents were elicited by 3 s voltage steps of −10 mV down to −120 mV. D, Current-voltage relationship for sodium current density ($I_{Na}$) in SANLCM and VLCM. Inset: voltage protocol, from a holding potential of −100 mV currents were elicited by 80 ms voltage steps of 5 mV up to +40 mV. Current densities were measured as peak inward currents. E,F, Analysis of barium ($Ba^{2+}$)-sensitive inward rectifier potassium current density ($I_{K1}$): Original traces of the barium sensitive inward rectifier potassium current component at different membrane potentials (E). Current-voltage relationship for barium-sensitive current density and average of maximum $I_{K1}$ current density at −120 mV in VLCM and SANLCM. (F). Inset: voltage protocol, from a holding potential of −40 mV currents were elicited by 3 s voltage steps of −10 mV down to −120 mV. T-test: *P<0.05 vs maximum current density in VLCM. Error bars show s.e.m.

Electrophysiological analyses revealed that SANLCM had significantly faster spontaneous action potential rates compared to VLCMs (FIG. 4A, B). Ninety percent of SANLCMs showed action potentials with typical pacemaker characteristics including slow maximum upstroke velocity (<30 V/s), small action potential amplitude and short action potential duration (FIG. 4C, Table 1). Additionally, SANLCMs contained significantly more pacemaker funny current ($I_f$) and less sodium current ($I_{Na}$), than the VLCMs (FIG. 4D, E and FIG. 9A-D). In addition, less inward rectifier potassium current ($I_{K1}$) was observed in SANLCMS, consistent with the hyperpolarized diastolic membrane potential of pacemaker cells (FIG. 9E, F).

To determine if SANLCMs could function as pacemakers, their ability to control the beating rate of VLCMs was tested. For these analyses, VLCMs were isolated by FACS and plated on a multi-electrode array (MEA) to form electrically integrated monolayers. Aggregates of SANLCMs or VLCMs (control) labeled with Tetramethylrhodamine methyl ester (TMRM) were placed at a specific site on these established VLCM monolayers. The combined aggregate/monolayer populations were cultured for a week to allow electrical integration (FIG. 4F). Analysis of electric signal propagation showed that, in the absence of any aggregates, the initiation site of electric activity in the monolayers changed randomly (FIG. 4G-I, FIG. 10A-C). In contrast, electric activity was stably initiated by the SANLCM aggregate (electrode 65) and propagated through the adjacent monolayer (FIG. 4J-L). As a result of this pacing activity, the beating frequency of the monolayer increased from 63.1±2.5 to 112.5±18.5 bpm (Table 2). In seventy-five percent of the experiments SANLCM were able to pace the VLCM monolayer for the 14-day duration of the experiment. Aggregates of VLCM did not show this pacing capacity, as initiation of electric activity remained random in these cultures (FIG. 10D-F).

During embryonic heart development FGF signaling secreted by the neural ectoderm is involved in the specification of NKX2-5$^+$ cardiac progenitors[26]. We reasoned that inhibition of FGF signaling could repress development of the NKX2-5$^+$ progenitors favoring the generation of the NKX2-5$^-$ SANLCMs. We therefore applied the FGF receptor inhibitor PD 173074 (Tocris) to our pacemaker differentiation conditions (BMP+RA) and found that inhibition of FGF signaling from day 4-6 results in an increase of NKX2-5$^-$cTNT$^+$ SANLCM from 33±1% to 48±3% in day 20 cultures. In contrast activation of FGF signaling using bFGF decreased the SANLCM population (12±1%). Importantly, application of the FGF inhibitor in a concentration ranging from 240-960 nM blocked the development of NKX2-5$^+$ cardiomyocytes (5±1% vs 35±5% at endogenous (e) bFGF levels e.g. no FGF added to the media). The block in development of NKX2-5$^+$ cardiomyocytes was most efficient when the FGF inhibitor was applied between day3-4 but had no effect when it was applied from day 5 onwards. This suggests that the NKX2-5$^+$ progenitor is specified around day 3-4, which correlates with the first detection of NK2-5:GFP$^+$ cells at day 6 of differentiation. (FIG. 12A-D).

Since the FGF inhibitor treated cultures only contain a small number of NKX2-5$^+$ cardiomyocytes it allows to isolate relatively pure populations of SANLCMs by selecting for SIRPA$^+$ and CD90$^-$ cardiomyocytes (76% post-sort purity for NKX2-5$^-$cTNT$^+$ SANLCMs) (FIG. 12E). Using this approach it should be possible to obtain highly enriched populations of SANLCMs from any human pluripotent stem cell line, independent of the NKX2-5:GFP transgene expression. As a proof of principle we applied our protocol to the HES-2 embryonic stem cell line. We specified the cardiac mesoderm using 2.5 ng/ml BMP and 0.5 µM RA in the presence of the FGF inhibitor. To analyze the cultures for the SANLCM proportion, at day 20 intracellular staining for NKX2-5 protein and cTNT followed by flow cytometric analysis was applied. For the HES2 line treatment with 240 nM FGFi from day3-5 obtained best results and generated cultures with up to 36% NKX2-5$^-$cTNT$^+$ SANLCMs and only a small proportion of NKX2-5$^+$ myocytes (5% vs 43% at endogenous bFGF levels) (FIG. 12F).

Human pacemaker cells have previously been isolated from hPSCs-derived cardiomyocyte populations using a cGata6 reporter[27]. Although the phenotype of these pacemaker cells was not specified they most likely resemble the secondary AVN pacemaker as the cGata6 reporter specifically marks the AVN in the mouse heart[28]. Here it is shown for the first time that pacemaker cells resembling the SAN can be isolated from hPSCs-derived cardiomyocyte populations using a NKX2-5:GFP reporter. Two novel signaling pathways BMP4 and RA that control SAN lineage specification were identified. The benefit of understanding pacemaker development is twofold because it also enables the elimination of contaminating pacemakers from hPSCs-derived ventricular populations where they could cause life-threatening arrhythmias upon transplantation into the heart. Accordingly, SANLCM present an attractive source for the generation of a biological pacemaker. Current approaches to a biological pacemaker include overexpression of pacemaker ion-channels and reprogramming of existing working cardiomyocytes[29,30]. It is suggested that hPSC-derived SANLCM represent a genuine biological pacemaker as they are generated by recapitulation of human development.

Example 2

Methods for In-vivo Transplantation and Ex Vivo Simultaneous ECG-recordings and Optical Mapping For the assessment of in vivo pacemaker capacity of SANLCM and VLCM, 8 adult Fischer-344 (200-300 g) rats were used. Animals were anesthetized (87 mg/kg Ketamine, 13 mg/kg Xylazine), intubated and mechanically-ventilated (100% $O_2$, 1 ml/kg volume). Following a left thoracotomy, 1-2×10⁶ SANLCM or VLCM (aggregated in low cluster 96 well plates at 80,000 cells/well) were injected into the left-ventricular anterior wall near the apex using a 28G needle. To prevent immune rejection of the human cell-grafts, animals were treated with cyclosporine A (13 mg/kg/day) and methylprednisolone (2 mg/kg/day).

For the optical mapping studies, at 14 days post-transplantation, hearts were harvested, transferred to a custom-built optical mapping chamber (allowing simultaneous electrocardiographic recordings and fluorescent voltage imaging) and retrogradely perfused using a Langendorff apparatus with oxygenized Tyrod's solution.

A unipolar electromyogram was recorded using a digital ECG data acquisition system (Biopac systems). A high-speed CCD-based optical mapping technique (Scimedia) was used to study the electrical activation patterns of the rat heart. To this end, the voltage-sensitive dye Di-4-ANB-DQBS (40 µL, 29.61 mMol/L) was added to the perfusate for loading prior to voltage mapping. Optical mapping was performed by illumination of the hearts with 1,000 watt quartz tungsten halogen lamp (Newport Corporation, USA), equipped with an electronic shutter and with an excitation filter of 660±10 nm (Chroma Technology Corp). Emission was measured using long-pass filter >715 nm (Edmund Optics) adjacent to the CCD camera.

A custom-based computer software (OMproCCD) was utilized for data analysis of the optical mapping signals. The data was viewed either as dynamic displays (movies) showing the propagation of the electric activation wavefronts or as activation maps. Activation (isochronal) maps were constructed by measuring the timing of electrical activation at each imaged-pixel (timing of the maximum dF/dt). The hearts were mapped at baseline (sinus-rhythm) and following application of Methacholine (1 µM, 0.1 ml) and Lidocaine (0.005% 0.1 ml) aiming to induce complete AV block and suppress the junctional escape rhythm.

The ability of SANLCMs to function as pacemaker in-vivo was tested by engrafting them as cell-aggregates into the apex of the rat heart. To evaluate the effect of cell transplantation 14 days later, optical mapping was performed using the isolated Langendorff-perfused heart model. The heart-rate of the rat is ~300 bpm, much faster than beating-rate of the human heart. A pharmacological approach was therefore developed (application of 0.1 ml Metacholine (1 µM)+Lidocaine (0.005%)) to induce transient complete atrioventricular (AV) block and suppress ventricular escape rhythm, in order to reveal potential pacemaker activity of the transplant. Using this approach three of three hearts that were injected with control VLCM demonstrated complete AV block with a junctional escape rhythm that slowed down to 76±4 bpm (FIG. 11A). Optical mapping confirmed that this endogenous slow escape rhythm was initiated at the septum (away for the area of cell transplantation) and then propagated to activate the rest of the ventricle (FIG. 11B). In contrast three out of three hearts that received the SANLCM transplant, displayed a significantly faster ventricular ectopic rhythm after induction of AV block (145±8 bpm). Optical mapping revealed that this new ectopic rhythm was initiated from the apex of the heart matching the transplantation site (FIG. 11C,D). The presence of the transplant and its ventricular/pacemaker identity was confirmed by immunostaining for human specific cTNT and MLC2v (FIG. 11E,F) Taken together these experiments provide the proof of principle that purified SANLCMs can act as biological pacemaker both in-vitro and in-vivo while VLCM have no pacemaker capacity.

TABLE 1

Electrophysiological characteristics of VLCM and SANLCM

| | N | Rate (bpm) | $dv/dt_{max}$ (V/s) | DMP (mV) | APA (mV) | APD50 (ms) | APD90 (ms) |
|---|---|---|---|---|---|---|---|
| VLCMs | 22 | 73.1 ± 6.3 | 115.9 ± 13.9 | −64.1 ± 1.7 | 121.6 ± 5.3 | 130.4 ± 13.8 | 194.3 ± 14.9 |
| SANLCMs | 19 | 133.1 ± 4.5** | 11.9 ± 3.1** | −55.8 ± 2.6** | 88.3 ± 2.9** | 65.4 ± 12.3** | 147.2 ± 13.1* |

APA, action potential amplitude;
APD50, action potential duration at 50% of repolarization;
APD90, action potential duration at 90% of repolarization;
DMP, diastolic membrane potential;
$dv/dt_{max}$, maximum action potential upstroke velocity;
N, cell number;
*P < 0.05,
**P < 0.01 vs VLCM

TABLE 2

Efficiency of VLCM and SANLCM aggregates to pace VLCM Monolayers

| Aggregates | N | Monolayer Rate before (bpm) | Aggregate Rate (bpm) | Electrical integration (n) | Pacing (n) | Pacing (%) | Monolayer Rate after (bpm) |
|---|---|---|---|---|---|---|---|
| VLCMs | 6 | 62.6 ± 2.1 | 53.5 ± 6.6 | 6 | 0 | 0% | 54.5 ± 10.7 |
| SANLCMs | 9 | 63.1 ± 2.5 | 142.2 ± 7.4** | 8 | 6 | 75% | 112.5 ± 18.5*[1] |

[1] Beating rates were only accounted for in successfully paced cultures.
Monolayer Rate before, beating rate of monolayer before placing the respective aggregate;
Monolayer Rate after, beating rate of monolayer after placing the respective aggregate;
N, cell number;
*P < 0.05,
**P < 0.01 vs VLCM Aggregates

TABLE 3

Primer Sequences

| Gene | Forward 5'-3' (SEQ ID NO) | Reverse 5'-3' (SEQ ID NO) |
|---|---|---|
| BRACHYURY (T) | TGTCCCAGGTGGCTTACAGATGA (1) | GGTGTGCCAAAGTTGCCAATACA (2) |
| cTNT | TTCACCAAAGATCTGCTCCTCGCT (3) | TTATTACTGGTGTGGAGTGGGTGTGG (4) |
| HCN1 | GCAGGCAATCGCTCCCATCAATTA (5) | TGTGTACACCGGTGGAGATTGTGT (6) |
| HCN4 | TCTTCCTCATTGTGGAGACACGCA (7) | TGAGGATCTTCGTGAAGCGGACAA (8) |
| IRX4 | TTGGACTCCTGGGAACATGGACAA (9) | ATGCTTCAGGGTATCTGGCCTCTT (10) |
| ISL1 | GAAGGTGGAGCTGCATTGGTT (11) | TAAACCAGCTACAGGACAGGCC (12) |
| KCNJ3 | TCATCAAGATGTCCCAGCCCAAGA (13) | CACCCGGAACATAAGCGTGAGTTT (14) |
| MESP1 | AGCCCAAGTGACAAGGGACA (15) | AAGGAACCACTTCGAAGGTGC (16) |
| MSX2 | GCGCAAGTTCCGTCAGAAACAGTA (17) | TTTGACCTGGGTCTCTGTGAGGTT (18) |
| MYL2 | TGTCCCTACCTTGTCTGTTAG (19) | ATTGGAACATGGCCTCTGGAT (20) |
| NKX2-5 | TTTGCATTCACTCCTGCGGAGACC (21) | ACTCATTGCACGCTGCATAATCG (22) |
| SCN5A | TGCTGCTCTTCCTCGTCATGTTCA (23) | TGTTGGCGAAGGTCTGGAAGTTGA (24) |
| SHOX2 | ATCGCAAAGAGGATGCGAAAGGGA (25) | TTCCAGGGTGAAATTGGTCCGACT (26) |
| TBP | TGAGTTGCTCATACCGTGCTG (27) | CCCTCAAACCAACTTGTCAACAG (28) |
| TBX2 | AACGCATGTACATCCACCCAGACA (29) | TTGTTGGTCAGCTTCAGCTTGTGG (30) |
| TBX3 | TTGAAGACCATGGAGCCCGAAGAA (31) | CCCGCTTGTGAAACTGATCCCAAA (32) |
| TBX5 | ACAAAGTGAAGGTGACGGGCCTTA (33) | ATCTGTGATCGTCGGCAGGTACAA (34) |
| TBX18 | TTAACCTTGTCCGTCTGCCTGAGT (35) | GTAATGGGCTTTGGCCTTTGCACT (36) |

While the present application has been described with reference to what are presently considered to be the preferred examples, it is to be understood that the application is not limited to the disclosed examples. To the contrary, the application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Specifically, the sequences associated with each accession numbers provided herein including for example accession numbers and/or biomarker sequences (e.g. protein and/or nucleic acid) provided in the Tables or elsewhere, are incorporated by reference in its entirely.

CITATIONS FOR REFERENCES REFERRED TO IN THE SPECIFICATION

1 Boyett, M. R., Honjo, H. & Kodama, I. The sinoatrial node, a heterogeneous pacemaker structure. *Cardiovascular research* 47, 658-687 (2000).
2 Monfredi, O., Dobrzynski, H., Mondal, T., Boyett, M. R. & Morris, G. M. The anatomy and physiology of the sinoatrial node—a contemporary review. *Pacing and clinical electrophysiology: PACE* 33, 1392-1406, doi: 10.1111/j.1540-8159.2010.02838.x (2010).
3 Nof, E., Glikson, M. & Antzelevitch, C. Genetics and Sinus Node Dysfunction. *Journal of atrial fibrillation* 1, 328-336 (2009).
4 Lau, D. H., Roberts-Thomson, K. C. & Sanders, P. Sinus node revisited. *Current opinion in cardiology* 26, 55-59, doi:10.1097/HCO.0b013e32834138f4 (2011).

5 Laflamme, M. A. et al. Cardiomyocytes derived from human embryonic stem cells in pro-survival factors enhance function of infarcted rat hearts. *Nature biotechnology* 25, 1015-1024, doi:10.1038/nbt1327 (2007).
6 Kattman, S. J. et al. Stage-specific optimization of activin/nodal and BMP signaling promotes cardiac differentiation of mouse and human pluripotent stem cell lines. *Cell stem cell* 8, 228-240, doi:10.1016/j.stem.2010.12.008 (2011).
7 Burridge, P. W. et al. Chemically defined generation of human cardiomyocytes. *Nature methods* 11, 855-860, doi:10.1038/nmeth.2999 (2014).
8 He, J. Q., Ma, Y., Lee, Y., Thomson, J. A. & Kamp, T. J. Human embryonic stem cells develop into multiple types of cardiac myocytes: action potential characterization. *Circulation research* 93, 32-39, doi:10.1161/01.RES.0000080317.92718.99 (2003).
9 Ma, J. et al. High purity human-induced pluripotent stem cell-derived cardiomyocytes: electrophysiological properties of action potentials and ionic currents. *American journal of physiology. Heart and circulatory physiology* 301, H2006-2017, doi:10.1152/ajpheart.00694.2011 (2011).
10 Elliott, D. A. et al. NKX2-5(eGFP/w) hESCs for isolation of human cardiac progenitors and cardiomyocytes. *Nature methods* 8, 1037-1040, doi:10.1038/nmeth.1740 (2011).
11 Park, I. H. et al. Reprogramming of human somatic cells to pluripotency with defined factors. *Nature* 451, 141-146, doi:10.1038/nature06534 (2008).
12 Kennedy, M., D'Souza, S. L., Lynch-Kattman, M., Schwantz, S. & Keller, G. Development of the hemangioblast defines the onset of hematopoiesis in human ES cell differentiation cultures. *Blood* 109, 2679-2687, doi:10.1182/blood-2006-09-047704 (2007).
13 Dubois, N. C. et al. SIRPA is a specific cell-surface marker for isolating cardiomyocytes derived from human pluripotent stem cells. *Nature biotechnology* 29, 1011-1018, doi:10.1038/nbt.2005 (2011).
14 Okada, Y. & SpringerLink (Online service). in *Springer Protocols Handbooks*, (Springer Japan, Tokyo, 2012).
15 Yang, L. et al. Human cardiovascular progenitor cells develop from a KDR+ embryonic-stem-cell-derived population. *Nature* 453, 524-528, doi:10.1038/nature06894 (2008).
16 Christoffels, V. M., Smits, G. J., Kispert, A. & Moorman, A. F. Development of the pacemaker tissues of the heart. *Circulation research* 106, 240-254, doi:10.1161/CIRCRESAHA.109.205419 (2010).
17 Mommersteeg, M. T. et al. The sinus *venosus* progenitors separate and diversify from the first and second heart fields early in development. *Cardiovascular research* 87, 92-101, doi:10.1093/cvr/cvq033 (2010).
18 Sizarov, A. et al. Molecular analysis of patterning of conduction tissues in the developing human heart. *Circulation. Arrhythmia and electrophysiology* 4, 532-542, doi:10.1161/CIRCEP.111.963421 (2011).
19 Christoffels, V. M. et al. Formation of the venous pole of the heart from an NKX2-5-negative precursor population requires Tbx18. *Circulation research* 98, 1555-1563, doi:10.1161/01.RES.0000227571.84189.65 (2006).
20 Christoffels, V. M. & Moorman, A. F. Development of the cardiac conduction system: why are some regions of the heart more arrhythmogenic than others? *Circulation. Arrhythmia and electrophysiology* 2, 195-207, doi:10.1161/CIRCEP.108.829341 (2009).
21 Horsthuis, T. et al. Gene expression profiling of the forming atrioventricular node using a novel tbx3-based node-specific transgenic reporter. *Circulation research* 105, 61-69, doi:10.1161/CIRCRESAHA.108.192443 (2009).
22 Witty, A. D. et al. Generation of the epicardial lineage from human pluripotent stem cells. *Nature biotechnology*, doi:10.1038/nbt.3002 (2014).
23 Xavier-Neto, J. et al. A retinoic acid-inducible transgenic marker of sino-atrial development in the mouse heart. *Development* 126, 2677-2687 (1999).
24 Rosenthal, N. & Xavier-Neto, J. From the bottom of the heart: anteroposterior decisions in cardiac muscle differentiation. *Current opinion in cell biology* 12, 742-746 (2000).
25 Pildner von Steinburg, S. et al. What is the "normal" fetal heart rate? *PeerJ* 1, e82, doi:10.7717/peerj.82 (2013).
26 Keren-Politansky, A., Keren, A. & Bengal, E. Neural ectoderm-secreted FGF initiates the expression of NKX2.5 in cardiac progenitors via a p38 MAPK/CREB pathway. *Developmental biology* 335, 374-384, doi:10.1016/j.ydbio.2009.09.012 (2009).
27 Zhu, W. Z. et al. Neuregulin/ErbB signaling regulates cardiac subtype specification in differentiating human embryonic stem cells. *Circulation research* 107, 776-786, doi:10.1161/CIRCRESAHA.110.223917 (2010).
28 Davis, D. L. et al. A GATA-6 gene heart-region-specific enhancer provides a novel means to mark and probe a discrete component of the mouse cardiac conduction system. *Mechanisms of development* 108, 105-119 (2001).
29 Li, R. A. Gene- and cell-based bio-artificial pacemaker: what basic and translational lessons have we learned? *Gene therapy* 19, 588-595, doi:10.1038/gt.2012.33 (2012).
30 Hu, Y. F., Dawkins, J. F., Cho, H. C., Marban, E. & Cingolani, E. Biological pacemaker created by minimally invasive somatic reprogramming in pigs with complete heart block. *Science translational medicine* 6, 245ra294, doi:10.1126/scitranslmed.3008681 (2014).

The invention claimed is:

1. A method of producing a population of cardiomyocytes, the method comprising:
   (a) incubating cardiovascular mesoderm cells in a cardiac induction medium comprising a WNT inhibitor, VEGF, or both for a period of time to generate cardiovascular progenitor cells that express NKX2-5; and
   (b) incubating the cardiovascular progenitor cells in a basic medium comprising VEGF for a period of time to generated a population of cardiomyocytes that are enriched for NKX2-5 $^{pos}$, cTNT$^{pos}$ cells.

2. The method of claim 1, wherein the cardiovascular mesoderm cells are generated from pluripotent stem cells (PSCs) according to the method:
   (a) incubating the PSCs in an embryoid body medium comprising a BMP component for a period of time to generate embryoid bodies; and
   (b) incubating the embryoid bodies in a mesoderm induction medium comprising a BMP component and an activin component for a period of time to generate cardiovascular mesoderm cells.

3. The method of claim 2, wherein the PSCs are human PSCs (hPSCs).

4. The method of claim 3, wherein the hPSCs are induced pluripotent stem cells (iPSCs) or human embryonic stem cells (hESCs).

5. The method of claim 3, wherein the hPSCs are hPSCs comprising a NKX2-5 reporter construct.

6. The method of claim 5, further comprising isolating a population of ventricular-like cardiomyocytes (VLCM) from the population of cardiomyocytes comprising
   selecting NKX2-5 positive cardiotnyocytes according to NKX2-5 reporter construct expression.

7. The method of claim 5, wherein the NKX2-5 reporter construct is a fluorescent NKX2-5 reporter construct.

8. The method of claim 1, wherein the cardiac induction medium comprises a WNT inhibitor.

9. The method of claim 8, wherein the cardiac induction medium further comprises VEGF.

10. The method of claim 9, wherein the WNT inhibitor is IWP2.

11. The method of claim 10, wherein the cardiac induction medium further comprises at least one of a FGF component and an activin/nodal inhibitor.

12. The method of claim 10, wherein the cardiac induction medium further comprises SR-431542.

13. The method of claim 10, further comprising the step of isolating the population of cardiomyocytes using a cardiomyocyte-specific surface marker or markers.

14. The method of claim 13 wherein the step of isolating the population of cardiomyocytes uses the markers signal-regulatory protein alpha (SIRPA) and thymocyte differentiation antigen 1 (THY-1/CD90).

15. The method of claim 2, wherein the embryoid body medium BMP component is BMP4 and the mesoderm induction medium BMP component is BMP4.

16. The method of claim 15, wherein the embryoid body medium further comprises a Rho-associated protein kinase (ROCK) inhibitor, the mesoderm induction medium activin component is Activin A, and the mesoderm induction medium further comprises bFGF.

17. The method of claim 12, wherein the cardiovascular mesoderm cells are generated from pluripotent stem cells (PSCs) according to the method:
   (a) incubating the PSCs in an embryoid body medium comprising a BMP component for a period of time to generate embryoid bodies; and
   (b) incubating the embryoid bodies in a mesoderm induction medium comprising a BMP component and an activin component for a period of time to generate cardiovascular mesoderm cells.

18. The method of claim 17, wherein the embryoid body medium BMP component is BMP4 and the mesoderm induction medium BMP component is BMP4.

19. The method of claim 18, wherein the embryoid body medium further comprises a Rho-associated protein kinase (ROCK) inhibitor, the mesoderm induction medium activin component is Activin A, and the mesoderm induction medium further comprises bFGF.

20. The method of claim 19, wherein the PSCs are human PSCs (hPSCs).

21. The method of claim 20, wherein the hPSCs are human induced pluripotent stem cells (hiPSCs) or human embryonic stem cells (hESCs).

22. The method of claim 7, wherein the fluorescent NKX2-5 reporter construct is a NKX2-5:GFP reporter construct.

* * * * *